US011364499B2

(12) United States Patent
Meller et al.

(10) Patent No.: US 11,364,499 B2
(45) Date of Patent: Jun. 21, 2022

(54) DEVICES AND METHODS FOR IMPROVED SINGLE-MOLECULE DETECTION

(71) Applicant: TECHNION RESEARCH & DEVELOPMENT FOUNDATION LIMITED, Haifa (IL)

(72) Inventors: Amit Meller, Haifa (IL); Moran Bercovici, Haifa (IL); Xander Frank Van Kooten, Haifa (IL); Joshua Spitzberg, Tel Aviv (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 244 days.

(21) Appl. No.: 16/613,462

(22) PCT Filed: May 15, 2018

(86) PCT No.: PCT/IL2018/050528
§ 371 (c)(1),
(2) Date: Nov. 14, 2019

(87) PCT Pub. No.: WO2018/211503
PCT Pub. Date: Nov. 22, 2018

(65) Prior Publication Data
US 2020/0171489 A1    Jun. 4, 2020

Related U.S. Application Data

(60) Provisional application No. 62/506,017, filed on May 15, 2017.

(51) Int. Cl.
*B01L 3/00* (2006.01)
*G01N 21/64* (2006.01)
(Continued)

(52) U.S. Cl.
CPC ...... *B01L 3/50273* (2013.01); *G01N 21/6486* (2013.01); *G01N 27/4145* (2013.01);
(Continued)

(58) Field of Classification Search
None
See application file for complete search history.

(56) References Cited

U.S. PATENT DOCUMENTS

2005/0121324 A1    6/2005  Park et al.
2006/0210995 A1    9/2006  Joyce
(Continued)

FOREIGN PATENT DOCUMENTS

EP         2878681 A1    6/2015
WO    2015181829 A1   12/2015
(Continued)

OTHER PUBLICATIONS

Merav Karsenty et al.: "Current monitoring in microchannel with repeated constrictions for accurate detection of sample location in isotachophoresis", Analytical Chemistry, vol. 87, No. 1, Jan. 6, 2015, pp. 388-393.
(Continued)

*Primary Examiner* — J. Christopher Ball
(74) *Attorney, Agent, or Firm* — The Roy Gross Law Firm, LLC; Roy Gross

(57) ABSTRACT

Devices for detecting a molecule of interest comprising an electrokinetic focusing apparatus and a nanopore apparatus are provided. Kits and systems comprising the apparatus are also provided; as are methods of detecting molecules of interest comprising running the molecules through the electrokinetic focusing apparatus and then detecting the focused molecules as they pass through the nanopore.

20 Claims, 9 Drawing Sheets

(51) Int. Cl.
    *G01N 27/414*     (2006.01)
    *G01N 27/447*     (2006.01)
    *G01N 33/487*     (2006.01)
    *G01N 33/543*     (2006.01)

(52) U.S. Cl.
    CPC ... *G01N 27/4473* (2013.01); *G01N 27/44721* (2013.01); *G01N 27/44791* (2013.01); *G01N 33/48721* (2013.01); *G01N 33/5438* (2013.01); *B01L 2200/0668* (2013.01); *B01L 2300/0663* (2013.01); *B01L 2300/0861* (2013.01); *B01L 2400/0421* (2013.01)

(56) References Cited

U.S. PATENT DOCUMENTS

| | | | |
|---|---|---|---|
| 2009/0136948 A1 | 5/2009 | Han et al. | |
| 2013/0175170 A1 | 7/2013 | Ivory | |
| 2015/0219594 A1* | 8/2015 | Vulto | G01N 27/447 204/549 |
| 2017/0022546 A1 | 1/2017 | Bashir et al. | |

FOREIGN PATENT DOCUMENTS

| | | | |
|---|---|---|---|
| WO | 2016161402 A1 | 10/2016 | |
| WO | 2016196625 A1 | 12/2016 | |
| WO | 2018065985 A1 | 4/2018 | |

OTHER PUBLICATIONS

Ortal Schwartz and Moran Bercovici: "Microfluidic assay for continuous bacteria detection using antimicrobial peptides and isotachophoresis", Analytical Chemistry, vol. 87, No. 20, Sep. 12, 2014, p. 10106-10113.

Kevin J. Freedman et al.: "Nanopore sensing at ultra-low concentrations using single-molecule dielectrophoretic trapping", Nature Communications, vol. 7, No. 1, Jan. 6, 2016, XP055747452.

Charles L. Asbury et al., "Trapping of DNA by dielectrophoresis", Electrophoresis, Issue 2002, vol. 23, pp. 2658-2666, 2002.

Min Jun Kim et al., "Rapid Fabrication of Uniformly Sized Nanopores and Nanopore Arrays for Parallel DNA Analysis", Advanced Materials, vol. 18 Issue 23 pp. 3149-3153, 2006.

Meni Wanunu et al., "Rapid electronic detection of probe-specific microRNAs using thin nanopore sensors", Nature Nanotechnology, vol. 5 Issue 11 pp. 807-814, 2010.

Wibke Hellmich et al. "Poly(oxyethylene) Based Surface Coatings for Poly(dimethylsiloxane) Microchannels", Langmuir, vol. 21 Issue 16 pp. 7551-7557, 2005.

Brett N. Anderson et al., "pH Tuning of DNA Translocation Time through Organically Functionalized Nanopores", ACS Nano, vol. 7, Issue 2 pp. 1408-1414, 2013.

Meni Wanunu, Amit Meller, "Chemically Modified Solid-State Nanopores", Nano Letters 7 Issue 6 pp. 1580-1585, 2007.

Petr Boček et al., "Recent developments in isotachophoresis", Journal of Chromatography, vol. 334 Issue 2 pp. 157-195, 1985.

Ralph M. M. Smeets et al., "Salt dependence of ion transport and DNA translocation through solid-state nanopores", Nano letters, vol. 6 Issue 1 pp. 89-95, 2006.

Tarun K. Khurana, Juan G. Santiago, "Sample zone dynamics in peak mode isotachophoresis", Anal Chem. Issue 80 vol. 16, 6300-6307, 2008.

PCT Search Report for International Application No. PCT/IL2018/050528 dated Sep. 13, 2018, 4 pp.

PCT Written Opinion for International Application No. PCT/IL2018/050528 dated Sep. 13, 2018, 7 pp.

PCT Preliminary Report on Patentability for International Application No. PCT/IL2018/050528, dated Nov. 19, 2019, 8 pp.

\* cited by examiner

DEVICES AND METHODS FOR IMPROVED SINGLE-MOLECULE DETECTION

CROSS REFERENCE TO RELATED APPLICATIONS

This application is a National Phase of PCT Patent Application No. PCT/IL2018/050528 having International filing date of May 15, 2018, which claims the benefit of priority of U.S. Provisional Patent Application No. 62/506,017, filed May 15, 2017, the contents of which are incorporated herein by reference in their entirety.

FIELD OF INVENTION

The present invention is in the field of single-molecule detection.

BACKGROUND OF THE INVENTION

Nanopore-based detection uses nanometric-scale orifices to detect and identify single molecules translocating across the pore, typically via an electric field. By processing a large number of single molecules, nanopore detection is known to achieve high specificity compared to traditional sensors which rely on single measurement of a large number of molecules. However, as the time between translocation events scales inversely with concentration, nanopore-based detection is limited in sensitivity when detecting rare/low-concentration analytes. Alternatively, as target concentration decreases, the time required for specific identification increases proportionally. This is an inherent limiting factor to nanopore based detection, as well as other single-molecule sensing technologies, limiting their use in clinical applications.

This limitation arises largely due to the small effective radius of molecule capture. Analytes freely diffuse through a sample volume until they enter the nanopore's capture region in which they are funneled by electrophoretic force to the nanopore. The typical scale of this capture region is on the orders of fL to pL (femoliters to picoliters), which is many orders of magnitude smaller than a sample volume of μL (microliters).

Biomolecular amplification methods are a well-known strategy to effectively bypass the limited sensitivity. However, these methods are expensive, suffer from limited multiplexibility, are prone to amplification errors and biases, and require substantial sample preparation time and biochemical reagents. Moreover, currently, biomolecular amplifications are restricted to nucleic acids (specifically to DNA). A method of locally increasing analyte concentration at the nanopore capture region, which is compatible with nanopore analysis is thus greatly needed.

Isotachophoresis (ITP) is an electrophoretic technique in which one or more target analytes are focused and separated based on differences in their effective electrophoretic mobility. ITP uses a discontinuous electrolyte system, in which part of the channel is filled with leading electrolyte (LE) and the remaining part is filled with terminating electrolyte (TE) (see, FIG. 1). Typically, a background electrolyte (also termed counter-ion), is also present throughout the system to ensure that the net charge is zero. The LE and TE are chosen in such a way that their effective electrophoretic mobility is higher and lower than that of the target analytes, respectively. The sample, containing the analytes, is initially located either at the interface between the LE and TE or mixed in with one of the two.

Once an electric field is applied, all ions electromigrate at a velocity equal to the product of their electrophoretic mobility and the local electric field. The interface which was initially present between the LE and TE is maintained by the difference in electrolyte mobilities, and continuity of current implies that a steep electric field gradient is established at the interface between the two electrolytes. Analyte ions with an intermediate mobility (i.e., with a mobility bracketed by that of the LE and TE), are focused at the LE/TE interface by this electric field gradient. The focusing ratio, a commonly used metric in ITP, quantifies the ratio of final (focused) to initial concentrations. By designing the chemistry of the LE and TE appropriately, a wide spectrum of target analytes can be selectively focused, ranging from small ionic compounds to large biomolecules such as nucleic acids.

SUMMARY OF THE INVENTION

The present invention provides devices for detecting a molecule of interest comprising an electrokinetic focusing apparatus and a nanopore apparatus. Kits and systems comprising the apparatus are also provided; as are methods of detecting molecules of interest comprising running the molecules through the electrokinetic focusing apparatus and then detecting the focused molecules as they pass through the nanopore.

According to a first aspect, there is provided a device for detecting a molecule of interest comprising:
  a. a nanopore apparatus, the nanopore apparatus comprising at least one ion-conducting nanopore;
  b. an electrokinetic focusing apparatus, the electrokinetic focusing apparatus comprising a microchannel, a first electrode and a second electrode, wherein the first and second electrodes are configured to produce an electric field in the microchannel;
  c. at least one sensor or capturing element configured for at least one of:
    i. detecting a position of the molecule of interest within the microchannel; and
    ii. capturing the molecule of interest in a region of the microchannel proximal to the nanopore;
wherein the electrokinetic focusing apparatus and the nanopore apparatus are in fluidic contact via the nanopore.

According to some embodiments, the electrokinetic focusing apparatus further comprises a first and a second fluidic reservoir connected by the microchannel and the first and second electrodes are configured to electrically contact fluid placed in the first reservoir and fluid placed in the second reservoir, respectively.

According to some embodiments, the nanopore apparatus further comprises a film, and wherein the film comprises the at least one ion-conducting nanopore. According to some embodiments, the nanopore apparatus further comprises a third fluidic reservoir and a third electrode configured to electrically contact fluid placed in the third reservoir. According to some embodiments, the electrokinetic focusing apparatus further comprising a fourth electrode configured to generate an electrical field with the third electrode.

According to some embodiments, the nanopore apparatus further comprises a detector configured to detect the single-molecule as it passes through the at least one nanopore. According to some embodiments, the detector is an optical detector or an electrical detector.

According to some embodiments, the ion-conducting nanopore is in a surface of the microchannel, or in a surface in the microchannel's interior. According to some embodiments, the nanopore is any one of a solid-state nanopore, self-assembled polymer nanopore, protein nanopore, or DNA nanopore.

According to some embodiments, the electrokinetic focusing apparatus is selected from an isotachophoresis (ITP) apparatus, a concentration polarization apparatus, an isoelectric focusing apparatus and a dielectrophoresis apparatus.

According to some embodiments, the molecule is selected from a double stranded DNA, a single stranded DNA, an RNA, a locked nucleic acid (LNA), a peptide nucleic acid (PNA), a Morpholino, a protein, an antibody, a metabolite, a polysaccharide, an exosome, or a combination thereof.

According to some embodiments, the detecting a position of the molecule of interest comprises at least one of:
a. directly detecting the molecule of interest or a moiety attached thereto;
b. optically detecting changes in a fluid in the microchannel; and
c. detecting electrical changes in the microchannel.

According to some embodiments, the moiety is a fluorochrome.

According to some embodiments, the optically detecting comprises detecting at least one of a fluorochrome in the fluid, a dye in the fluid, absorbance of the fluid, refraction of the fluid, and interference of the fluid.

According to some embodiments, the detecting electrical changes comprises detecting at least one of, voltage, current, resistance, conductivity and impedance in the microchannel.

According to some embodiments, the capturing comprises closing off the region proximal to the nanopore from a remainder of the microchannel. According to some embodiments, the capture element comprises at least 2 valves proximal to the nanopore, wherein the valves are configured to enclose fluid in the microchannel proximal to the nanopore. According to some embodiments, the capture element comprises an element that binds the molecule of interest or a moiety attached thereto. According to some embodiments, a region of the capturing element, or the moiety attached thereto, is configured to be cleaved.

According to some embodiments, the sensor or capture element is configured to turn off the electric field produced by the first and second electrodes, when the molecule of interest is proximal to the nanopore.

According to some embodiments, proximal to the nanopore is within 100 microns (μm) of the nanopore.

According to some embodiments, the fluid in the first reservoir is an electrolyte solution of effective ion mobility higher than the molecule of interest (LE) and the fluid in the second reservoir is an electrolyte solution of effective ion mobility lower than the molecule of interest (TE). According to some embodiments, the LE comprises between 50 and 500 mM of monovalent strong base cations. According to some embodiments, the cations are selected from potassium ions (K+) sodium ions (Na+) and lithium ions (Li+).

According to some embodiments, the microchannel is configured such that the nanopore is sufficiently distanced from the first and second electrodes to allow for at least an 100× increase in concentration of the molecule of interest in a region proximal to the nanopore as compared to a concentration of the molecule of interest when deposited in the device.

According to some embodiments, the device of the invention further comprises a closing and locking mechanism for adhering the electrokinetic focusing apparatus to the nanopore apparatus in a water-tight fashion.

According to some embodiments, at least one surface of the electrokinetic focusing apparatus is treated with a compound that modulates the electroosmotic flow of fluid in the microchannel.

According to some embodiments, the microchannel comprises a tapered region comprising a decreasing volume as it approaches the hole and the sensor detects electrical changes caused by fluid flow through the tapered region.

According to some embodiments, the device of the invention further comprises an element that electrically connects the microchannel to the third reservoir. According to some embodiments, the element comprises a fourth reservoir and the fourth reservoir is electrically connected, but not fluidically connected, to the third reservoir. According to some embodiments, the element comprises a second microchannel and wherein the second microchannel fluidically connects the first microchannel to the third reservoir or the fourth reservoir. According to some embodiments, the element comprises a power source configured to provide an electric filed to induce movement of the molecule of interest through the nanopore.

According to some embodiments, the device of the invention further comprises a fast-acting switch configured to switch from conducting current between the first and second electrodes and conducting current between the third electrode and another electrode. According to some embodiments, the fast-acting switch produces output noise that is not more than 30% of a nanopore measuring signal. and high electric isolation. According to some embodiments, the fast-acting switch is selected from an optically isolated metal oxide semiconductor field effect transistor (OPFET) switch and a bipolar junction (BPJ).

According to some embodiments, the device of the invention further comprises a mechanism for inducing counterflow in a direction opposite to a direction of the focusing. According to some embodiments, the mechanism is configured to activate pressure driven flow or electroosmotic flow.

According to another aspect, there is provided a method for single-molecule detection of a molecule of interest, the method comprising electrokinetically focusing the molecule of interest to a location proximal to a nanopore, inducing the movement of the molecule of interest through the nanopore and detecting the molecule of interest as it passes through the nanopore, thereby detecting single molecules of a molecule of interest.

According to another aspect, there is provided a method for improving the function of a single molecule detection apparatus, the method comprising fluidically connecting the single molecule detection apparatus to an electrokinetic focusing apparatus.

According to some embodiments, the electrokinetically focusing comprises
a. loading a device of the invention with a first electrolyte solution of effective ion mobility higher than the molecule of interest (LE) into the first reservoir, a second electrolyte solution of effective ion mobility lower than the molecule of interest (TE) into the second reservoirs and the microchannel and a third electrolyte solution of conductivity equal to or greater than the conductivity of the TE and the LE into the third reservoir;
b. adding a solution comprising the molecule of interest to any one of:
   i. the TE,
   ii. the LE, and
   iii. a contact zone between the TE and the LE;

c. running direct current between the first and the second electrodes for a period of time sufficient for the molecule of interest to be proximal to the nanopore.

According to some embodiments, the method of the invention further comprises halting the movement of the molecule in the direction of the first and second electrodes while proximal to the nanopore.

According to some embodiments, the halting comprises at least one of:
a. removal of the direct current;
b. enclosing the area proximal to the nanopore;
c. activating counter-flow in a direction opposite to the movement; and
d. capturing the molecule or a moiety attached thereto to a capture element in a region proximal to the nanopore.

According to some embodiments, the activating counter-flow comprises using pressure driven flow or electroosmotic flow.

According to some embodiments, the method of the invention further comprises releasing the molecule from the capture element. According to some embodiments, the releasing comprises cleaving the capture element or the moiety.

According to some embodiments, the LE comprises between 50 and 500 mM of monovalent strong base cations. According to some embodiments, the cations are selected from potassium ions (K+) sodium ions (Na+) and lithium ions (Li+). According to some embodiments, the LE comprises a conductivity of between 0.5 and 10 S/m. According to some embodiments, the third electrolyte solution comprises at least the concentration of the monovalent strong base cations as the LE.

According to some embodiments, the electrokinetic focusing apparatus increases the concentration of the molecule of interest at the nanopore by between 100 and 1000000-fold as compared to a concentration of the molecule of interest at the nanopore when the nanopore apparatus is used alone.

According to some embodiments, the inducing comprises running direct current from an electrode to the third electrode and the halting and inducing are synchronized by the fast-acting switch.

According to another aspect, there is provided a kit comprising,
a. a device of the invention,
b. a solution of high effective mobility leading electrolyte (LE) ion, and
c. a solution of low effective mobility leading electrolyte (TE) ion.

According to some embodiments, the kit of the invention further comprises at least one of: a DNA probe, a peptide nucleic acid (PNA) probe, a Morpholino probe, a protein probe, and a combination thereof. According to some embodiments, the probes are fluorescently labeled.

According to another aspect, there is provided a system comprising,
a. a device of the invention, and
b. at least one direct current power source for generating an electric field between electrodes of the device.

According to some embodiments, the system further comprises a second direct power source, wherein the first power source is configured to generate an electric field between the first and second electrodes and the second power source is configured to generate an electric field between an electrode and the third electrode.

According to some embodiments, the system of the invention further comprises a control unit or computer for performing at least one of,
a. monitoring a position of the molecule of interest within the microchannel;
b. stopping current running between the first and second electrodes;
c. activating current between an electrode and the third electrode;
d. capturing the molecule of interest proximal to the nanopore;
e. releasing a molecule of interest captured proximal to the nanopore and
f. analyzing the molecule of interest as it passes through the nanopore.

According to some embodiments, the analyzing comprises sequencing of the molecule.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION

Figure 1A:
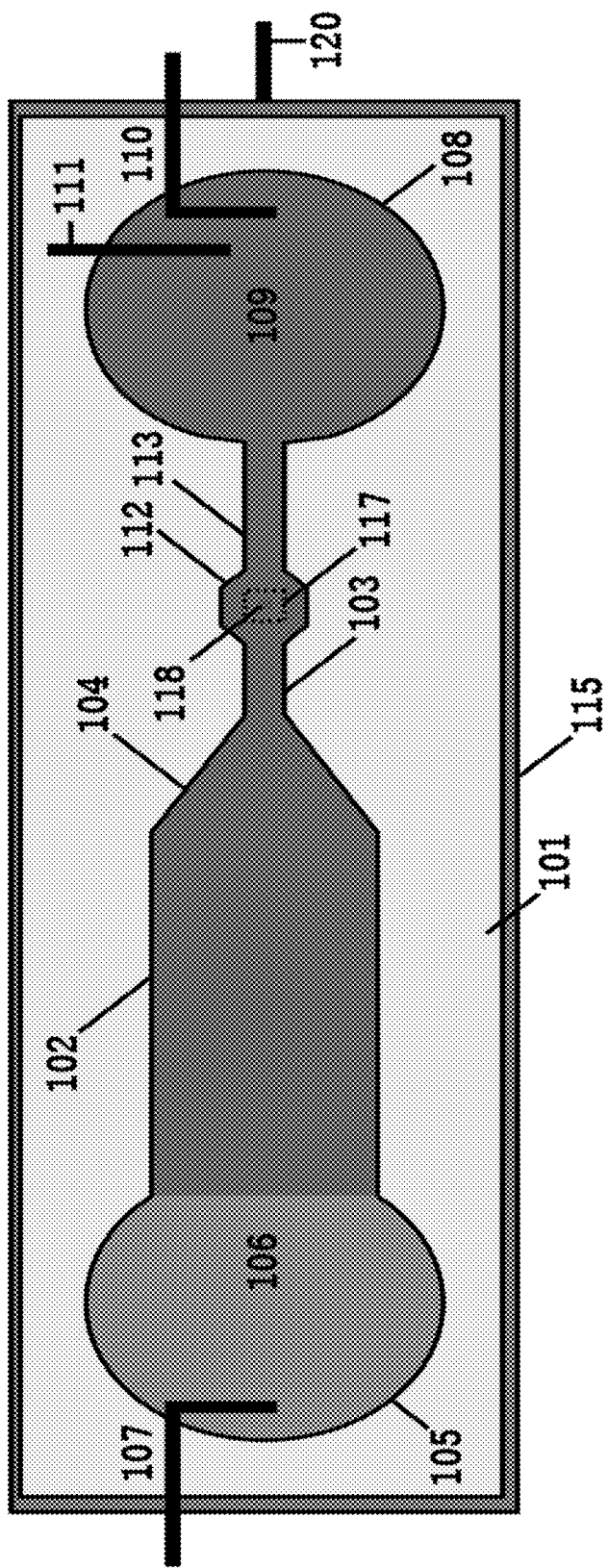
FIGS. 1A-C: A schematic drawing of the device/system of the invention. (1A) An aerial view of the microfluidics layer 101. (1B) A side view of the device/system including the microfluidics lay and the nanopore device layer. (1C) An aerial view as in 1A, but after the ITP has been run such that the concentrated molecules 119 are in proximity to nanopore 118.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Some embodiments of the present invention may be related to a device or system for improved detection of target molecules within a solution. Specifically, the device or system is useful in the detection of molecules at a low concentration in the solution, and for improving the efficiency and accuracy of single-molecule detection. The device or system employs electrokinetic focusing to concentrate target biomolecules directly adjacent to a nanopore transducer, specifically within a distance such that the biomolecules are within the capture region of the nanopore. Furthermore, by focusing sample from the microliter-scale dimension of the sample, into micron-scale zones, the device effectively bridges this size-mismatch limit in nanopore sensing.

Electrokinetic focusing methods are useful means of increasing the (local) concentration of charged biomolecules, including nucleic acids, proteins, antibodies, and metabolites. Importantly, they focus and concentrate the original molecules present in a sample, rather than introduce/copy/create new ones by an imperfect amplification process. In particular, isotachophoresis (ITP) is very effective, as it is able to work on inhomogeneous samples by selecting TE and LE that bracket the mobility of just the target molecules. Further, this method accelerates the translocation rate through the nanopore, and hence the sensitivity of the detection. Further advantages of the invention are that it does not require sample preparation (no off-chip lysis), has no mechanical parts, can be applied directly to analytes such as blood/serum, and allows operation and analysis at extremely low sample concentrations and clinically relevant time-scales.

However, there is substantial difficulty in marrying the ITP technology to the nanopore technology. Both require electrical fields to move the target molecules, however, the fields are of different strengths and often in different directions. Further, a nanopore requires high ionic strength at the cis side of the nanopore, however high ionic strength results in reduced mobility during ITP and an increased temperature during sample movement, both of which are detrimental to the desire to improve the molecule sensing. In the same vein, conductivity on the cis side of the nanopore must be high to enable detection, but this is once again detrimental to ITP functionality. Further, nanopore detection typically makes use of high concentrations of salts such as KCl or NaCl, which are detrimental to ITP functionality if present in the TE buffer. Lastly, the nanopore capture region is very small, on the order of 1-100 microns, whereas the variance in run rate of ITP, especially with analyte samples of varying makeup, is beyond this measure. When current traces from a device with a constriction are compared, the time it takes the molecule of interest to arrive at the nanopore varies on the order of 1-10 seconds. At an ITP velocity on the order of 100 um/s, this translates to a positioning inaccuracy of 100 um-1 mm, far greater than the capture area of a nanopore. As such, running of the ITP system for a given time will not place the interface, where the concentrated molecules are located, directly adjacent to the nanopore. Rather it is necessary for the device or system to also have a means of determining the position of the interface so that translocation through the nanopore can be activated when the molecules are within only a few microns of the nanopore.

Reference is now made to the drawings. FIG. 1A shows a schematic illustration of the device and/or system. A microfluidic layer (101) comprises a microchannel consisting of a first channel section (102) having a first cross-sectional area, joined internally to a second channel section (103) having a second cross-sectional area. In some embodiments, the first cross-sectional area of the channel may be larger than the second along at least one dimension, in which case the regions (102) and (103) are joined by a third converging section (104) having a tapering cross-sectional area. The microfluidic layer can be made of polymers such as polydimethylsiloxane (PDMS), polymethyl methacrylate (PMMA), cyclic olefin copolymer (COC), inorganic materials such as glass, or other materials in which the fabrication of microchannels is known to those skilled in the art. The microfluidics layer will be fully sealed such that there is not leakage and will be one continuous layer such that fluid and analyte can more freely throughout.

As the concentration of target analytes after ITP focusing is proportional to the length of the microchannel (102+103 and optionally 104), the channel should be as long as possible within any other constraints that may limit the length. In some embodiments, the length of the microchannel is at least 1, 2, 3, 4, or 5 centimeters. Each possibility represents a separate embodiment of the invention. In some embodiments, the ITP can be run in a matter of minutes. In some embodiments, the ITP is run with applied voltages between 100 and 1000 volts (V). In some embodiments, the length of the microchannel is configured to complete a run in a desired time at a desired applied voltage. For lower voltages and/or shorter times the length may be shorter. For higher voltages and/or longer times the length may be longer. For competition of runs in a matter of minutes and with an applied voltage of 100-1000 V, the channel has a length of several centimeters. In some embodiments, the length of the microchannel is not more than 7, 10, 12, 15, 17, 20, 25 or 30 cm. Each possibility represents a separate embodiment of the invention. In some embodiments, the length of the microchannel is sufficient to allow for electrokinetic focusing.

The width and height of section 102 may be equal to or greater than section 104. The height of sections 102, 104 and 103 may decrease abruptly or be tapered so as to reduce gradually. The depth of the microchannel as it reaches a nanopore 118 should be equal to or less than the capture region of nanopore 118 or a nanopore array located in chamber 112. If the microchannel is too tall, molecules in the upper region of the microchannel may not be focused close enough to the nanopore. The width of the channel 103 corresponds to the capture region of nanopore 118 or a nanopore array located in chamber 112. Though the width of 103 need not be equal to the width of the nanopore capture area it should be close to this size so that there is not a large change between section 103 and chamber 112. As used herein, "capture radius" refers to the distance from the nanopore aperture wherein the effect of electrophoresis overcomes free diffusion of molecules. In some embodiments, the nanopore capture area extends between 1 and 500, 1 and 400, 1 and 300, 1 and 200, 1 and 100, 5 and 500, 5 and 400, 5 and 300, 5 and 200, 5 and 100, 10 and 500, 10 and 400, 10 and 300, 10 and 200, or 10 and 100 µm away from the nanopore. In some embodiments, the capture area extends between 10 and 100 µm away from the nanopore. Each possibility represents a separate embodiment of the invention. In some embodiments, the nanopore capture area extends at most 10, 20, 30, 40, 50, 60, 70, 80, 90, 100, 120, 140, 150, 160, 180, 200, 220, 240, 250, 260, 280, 300, 320, 340, 350, 360, 380, 400, 420, 440, 450, 460, 480 or 500 µm away from the nanopore. Each possibility represents a separate embodiment of the invention. In some embodiments, a region proximal to the nanopore is a region within the nanopore capture area. In some embodiments, a proximal region is within 10, 20, 30, 40, 50, 60, 70, 80, 90, 100, 120, 140, 150, 160, 180, 200, 220, 240, 250, 260, 280, 300, 320, 340, 350, 360, 380, 400, 420, 440, 450, 460, 480 or 500 µm away from the nanopore. Each possibility represents a separate embodiment of the invention. In some embodiments, a proximal region is within 100 μm of the nanopore. In some embodiments, the cross-sectional area of 112 is larger than the cross-sectional area of 103. In some embodiments, the cross-sectional area of 112 is smaller than or equal to that of 103. This may be done for the purpose of locally increasing the electrical resistance of the microchannel, thus increasing the local electric field strength and causing further concentration enhancements in isotachophoresis.

When section 104 is present the change in cross sectional area can be small (<10× change) or large (>10× change). In some embodiments, the tapering is not a step (90-degree tapering). In some embodiments, the change in cross sectional area is less than a decrease of 100:1, 50:1, 30:1, 20:1, 10:1, 7:1, 5:1, 3:1 or 2:1. Each possibility represents a separate embodiment of the invention. In some embodiments, the angle of tapering is at least 1, 2, 3, 5, 10, 15, 20, 15, 30, 35, 40, or 45 degrees. Each possibility represents a separate embodiment of the invention. In some embodiments, the angle of tapering is at most 25, 30, 35, 40, 45, 50, 55, 60, 65, 70, 75, or 80 degrees. Each possibility represents a separate embodiment of the invention. In some embodiments, the angle of tapering is between 5-45, 5-40, 5-35, 5-30, 10-40, 10-35, 10-30, 15-45, 15-40, 15-15, 15-30, 20-45, 20-40, 20-35, 20-30, 25-25, 25-40, 25-35, and 25-30 degrees. Each possibility represents a separate embodiment of the invention. In some embodiments, the angle of tapering is about 30 degrees. Details concerning tapered regions in an electrokinetic focusing apparatus, and the ability to use them to detect the interface are provided in WO2015181829 and WO2018065985, both of which are herein incorporated in their entireties by reference. In some embodiments, the passing of the interface through a tapering channel causes changes in electrical current that allow for detection of the position and/or movement of the interface. In embodiments, where the device is run with a constant voltage, current in the microchannel can be measured. The tapering generates a change in electrical resistance in the microchannel when the interface passes through. By measuring the rate of decrease in current in the microchannel it can be determined when the interface passes through the tapered (narrowed) area. If the tapering continues until the nanopore monitoring of the rate of decrease in current can inform when the interface has reached the nanopore. If the tapering stops or is only for a portion of the microchannel, by knowing when the interface is in the tapered region it can extrapolated when the interface (and the molecules of interest) will reach the nanopore. This detection can be performed by a dedicated sensor in the channel or by one of electrodes 107 or 110. In some embodiments, the electrical detection is by electrode 110. In some embodiments, the electrical detection is by electrode 107.

At both ends of the microchannel, reservoirs (105) and (106) provide external access to the microchannel. The size of the reservoirs is variable. In some embodiments, the 105 is configured to hold at least 1, 2, 3, 5, 10, 15, 20, 25, 30, 35, 40, 45, 50 75, 100, 150, 200, 250, 300, 350, 400, 450, or 500 ul of fluid. Each possibility represents a separate embodiment of the invention. In some embodiments, the 106 is configured to hold at least 1, 2, 3, 5, 10, 15, 20, 25, 30, 35, 40, 45, 50 75, 100, 150, 200, 250, 300, 350, 400, 450, or 500 ul of fluid. Each possibility represents a separate embodiment of the invention.

Reservoir 105 is configured such that when a fluid is placed therein the fluid is contacted by separation cathode 107. Reservoir 106 is configured such that when a fluid is placed therein the fluid is contacted by separation anode 110.

Electrodes 107 and 110 are configured to generate an electrical field in the fluidics layer to induce isotachophoresis. Optionally, there is a third electrode 111 for generating an electric field in the Z direction, to enable translocation through the nanopore. In some embodiments, electrode 107 and or 110 is configured for this purpose. Electrode 111 is shown within reservoir 109 but need not be located there. Electrode 109 can be located anywhere where it can contact the fluids within layer 101 Electrode 120 is located on the trans side of the nanopore (the non-microfluidics side) and is required for inducing translocation through the nanopore. In some embodiments where electrode 111 is a separate electrode from 107 and 110, electrode 111 is a floating electrode. In some embodiments, electrode 111 is narrow such as to not be damaged by the electric field generated by 107 and 110. The electric field in the channel induces a potential on a (floating) electrode—since the electrode is a conductor, its potential is uniform throughout its length. At the same time, the potential in the channel varies monotonically from one electrode to the other. As a result, there exists a potential difference between the electrode and the fluid, which is at its maximum at two tips of the electrode. If this potential difference is higher than the required overpotential, oxidation and reduction would occur at the anode and cathode respectively, resulting in formation of gas bubbles which would ultimately block the channel and disrupt ITP. It is therefore necessary that the electrode have a geometry and/or dimensions that are compatible with the application of high electric fields. The width of the electrode (in the direction of the field generated by 107 and 110) must be small enough such that the electric field (E) multiplied by the width of the electrode (d) is not more than 1 volt (E×d≤0.1 or d≤0.1/E). Electric fields used in ITP are of order 1E3-1E4 V/m, and the voltage required to initiate electrolysis is of order 1 V. If for example the electric field is equal to 100 V/cm, then the width of the electrode must not exceed 100 μm. For a higher electric field, the electrode must be even smaller.

The electrodes can be activated and deactivated simultaneously, individually or in groups (or example 107 and 110 together, and 111 and 120 together). In some embodiments, the electrodes are made of and/or coated with a noble metal, or a noble metal containing compound. In some embodiments, the noble metal is selected from platinum (Pt), silver (Ag), ruthenium (Ru), rhodium (Rh), palladium (Pd), osmium (Os), iridium (Ir), and gold (Au). In some embodiments, the noble metal is Pt. In some embodiments, the noble metal is Ag. In some embodiments, the electrode is made of and/or coated with silver and/or silver chloride (AgCl). Optionally, electrodes 107 and 110 are connected to a computer-controlled power supply. In some embodiments, the power supply is capable of providing the required DC separation voltage. In some embodiments, the power supply is the Keithley 2410.

In some embodiments, the electrodes are connected to a fast-acting switch. When the electric field applied during ITP is turned off, diffusion of the focused analyte zone causes the concentration of analyte to decrease. In order to achieve the highest possible detection sensitivity, nanopore sensing should be initiated as soon as possible after the focused analyte zone is delivered to the nanopore. The fast-acting switch can switch from generating an electrical field between electrodes 107 and 110 (focusing electrodes) and generating an electrical field for translocation through the nanopore. Fast-acting switches are known in the art, and non-limiting examples of such include optically isolated metal oxide semiconductor field effect transistor (OPFET)

relays and bipolar junctions (BPJs). In some embodiments, the fast-acting switch comprises an OPFET. OPFETs have low output noise (capacitance on the order of 1-10 pF, resistance 1-100 Ohm), which is small with respect to the nanopore measurement signal and provide good electrical isolation (resistance on the order of 1 GOhm or larger, capacitance on the order of 1 pF or smaller) to ensure the signal used to control the OPFET state is sufficiently isolated from the measurement signal. In some embodiments, the fast-acting switch produces output noise that is not more 1, 5, 10, 15, 20, 25, 30, 35, 40, 45, 50, 60, 70, 80 or 90% of the nanopore measurement signal. Each possibility represents a separate embodiment of the invention. In some embodiments, the fast-acting switch is electrically isolated from the nanopore measurement signal.

In alternative embodiments, more than two reservoirs may be used, for instance with the purpose of focusing a finite amount of sample through a process known as electrokinetic injection (EKI) or finite-injection focusing. Such modifications do not affect the overall functionality of the invention and can be designed by those skilled in the art, given the aforementioned and without knowledge of undisclosed prior art.

Channel 103 is connected to the nanopore 118 containing chamber 112. Chamber 112 is connected to a third channel section 113 that continues until reservoir 109. The cross-sectional area of section 113 does not affect the performance of the device and may therefore be chosen arbitrarily. In some embodiments, section 113 is straight. In some embodiments, section 113 is parallel to section 103. In some embodiments, section 113 is a continuation of section 103, with chamber 112 in between. In some embodiments, chamber 112 is configured such that fluid within the chamber is within the capture area of nanopore 118, or an array of nanopores 118. For simplicity, going forward reference will be made to a single nanopore 118, but a skilled artisan will understand that an array of nanopores can be made within chamber 112 to facilitate increased sensing and molecule identification. Nanopore arrays are well known in the art and scaling up from a single nanopore to an array is well known in the art. Nanopore 118 is within a free-hanging membrane 117 which will be further discussed herein below. Nanopore 118 may also be within the wall of the microchannel. Nanopore 118 may also be in any surface of the microchannel. Nanopore 118 may also be within a wall that structurally defines the boundaries of the microchannel. Nanopore 118 may also be in a surface within the microchannel. That is a surface within the lumen or interior of the microchannel. This other surface within the microchannel need not be a part of the microchannel, nor need it define the microchannel structurally. Optionally, there may be a raised surface within the microchannel and the nanopore may be within this raised surface. The surface may be raised at least 1, 2, 3, 5, 7, 10, 12, 15, 17, 20, 25 or 30 μm away from a wall of the microchannel.

In some embodiments, the film comprises at least one nanopore. In some embodiments, the film comprises at least 2 nanopores. In some embodiments, the film comprises a plurality of nanopores. In some embodiments, the film comprises an array of nanopores. In some embodiments, the array comprises dimensions of 5×5, 5×10, 5×15, 5×20, 5×25, 5×30, 5×35, 5×40, 5×45, 5×50, 10×10, 10×15, 10×20, 10×25, 10×30, 10×35, 10×40, 10×45, 10×50, 15×15, 15×20, 15×25, 15×30, 15×35, 15×40, 15×45, 15×50, 20×20, 20×25, 20×30, 20×35, 20×40, 20×45, 20×50, 25×25, 25×30, 25×35, 25×40, 25×45, 25×50, 30×30, 30×35, 30×40, 30×45, 30×50, 35×35, 35×40, 35×45, 35×50, 40×40, 40×45, 40×50, 45×45, 45×50, or 50×50 μm. Each possibility represents a separate embodiment of the invention. In some embodiments, the array comprises dimensions of 30 μm by 30 μm. In some embodiments, the nanopores are separated by about 1 μm. In some embodiments, the nanopores are separate by at least 1, 1.5, 2, 2.5, 3, 3.5, 4, 4.5, 5, 6, 7, 8, 9 or 10 μm. Each possibility represents a separate embodiment of the invention. In some embodiments, the nanopores are separated by at least 1 μm.

In some embodiments, the width and length of chamber 112 is configured such that the cross-sectional area is equal to or smaller than the capture area of nanopore 118. In some embodiments, the height of chamber 112 is configured such that it does not exceed the capture distance of nanopore 118. In some embodiments, the device comprises valves that can close off chamber 112. These valves allow for capture of the interface, and the desired molecules, within chamber 112. The valves also halt the movement of the molecules of interest. In some embodiments, the valves enclose an area corresponding to the capture area of the nanopore. In embodiments comprising valves that close chamber 112, electrode 111 must be inside chamber 112 in order to facilitate translocation through the nanopore.

Figure 1B:
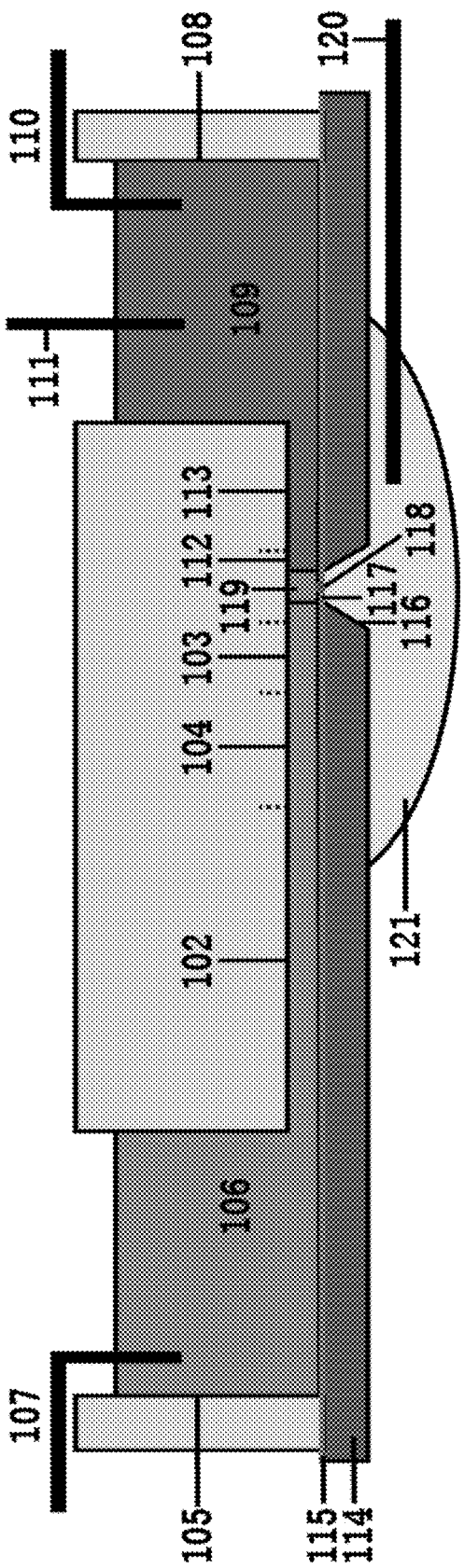

Reference is now made to FIG. 1B. FIG. 1B is a side view of the device shown from above in FIG. 1A. The microfluidic layer 101 is placed on and fluidically sealed against a solid-state nanopore device layer, typically consisting of a carrier substrate 114 coated on one side with a thin film 115. Microfluidic layer 101 may comprise a block of dead space that results in channels 102, 103, 104, 112 and 113 having a decreased height as compared to reservoirs 106 and 109. Having a channel that is short in the Z direction forces the desired molecules at interface 119 to be close to nanopore 118. In some embodiments, the height of the channel is uniform across sections 102, 103, 104 and 112. In some embodiments, the height of the channel tappers down as it moves from toward chamber 112. In some embodiments, the height of the channel is between 10-500, 10-100, 10-50, 20-500, 20-100, 20-50, 30-500, 30-100, 30-50, 40-500, 40-100, or 40-50 μm. Each possibility represents a separate embodiment of the invention. In some embodiments, the height of the channel is not more than the capture area of the nanopore. In some embodiments, the height of the channel is not more than 100 μm. In some embodiments, the carrier substrate is a wafer. In some embodiments, the carrier substrate is made of silicon. In some embodiments, the wafer is a crystal orientation wafer. In some embodiments, the carrier substrate is thicker in regions that lack a nanopore. In some embodiments, the carrier substrate comprises a thickness of at least 50, 100, 150, 200, 250, 300, 350 or 400 μm. Each possibility represents a separate embodiment of the invention.

Film 115 is on the cis (microfluidic) side of the nanopore device layer. The trans side is thus the side away from the layer 101. As used herein, the terms "film" and "membrane" are used interchangeably and refer to a thin layer of material. In some embodiments, film 115 is dielectric. In some embodiments, the film comprises silicon. In some embodiments, the film is silicon based. In some embodiments, the film comprises silicon nitride (SiNx). In some embodiments the film comprises a metal oxide. In some embodiments, the metal oxide is selected from aluminum oxide ($AlO_2$), titanium oxide ($TiO_2$), silicon oxide ($SiO_2$) and halfnium oxide ($HfO_2$). In some embodiments, the film has a universal thickness. In some embodiments, the film has a constant thickens across its entire area. In some embodiments, the film has a variable thickness. In some embodiments, the film is thinner in the area of the nanopore. In some embodiments, the film comprises a thickness of less than 500, 450, 400, 350, 300, 250, 200, 150, 100, 75, 50, 25, 20, 15, 10, 5, 4, 3, 2, or 1 nm. Each possibility represents a separate embodiment of the invention. In some embodiments, the film comprises a thickness of less than 100 nm. In some embodiments, the film comprises a thickness of about 25 nm. In some embodiments, the film comprises a thickness of about 10 nm. In some embodiments, film 115 has a thickness of between 0.5-100 nm.

The production of nanopores in a film is well known in the art. Fabrication of nanopores in thin membranes has been shown in, for example, Kim et al., Adv. Mater. 2006, 18 (23), 3149 and Wanunu, M. et al., Nature Nanotechnology 2010, 5 (11), 807-814. In some embodiments, the nanopore is produced with a transition electron microscope (TEM). In some embodiments, the nanopore is produced with a high-resolution aberration-corrected TEM or a noncorrected TEM. Carrier substrate 114 can be a wafer, or a larger counterpart thereof. Solid substrates for construction of nanopores are well known in the art. Indeed, the nanopore device layer of the invention can comprise any nanopore known in the art and is not limited to the exemplary nanopore device described herein. Substrate 114 has an etched window region 116 where the carrier substrate material is removed throughout the thickness of the device so that the thin film 115 is exposed in a free-hanging membrane 117.

In some embodiments, window region 116 comprises a cross-sectional area at the surface of substrate 114 of about 500 μm². In some embodiments, window region 116 comprises a cross-sectional area at the surface of substrate 114 of at least 100, 200, 300, 400, or 500 μm². Each possibility represents a separate embodiment of the invention. In some embodiments, window region 116 comprises a cross-sectional area at the surface of substrate 114 of at most 400, 500, 600, 700, 800, 900, 1000, 1500 or 2000 μm². Each possibility represents a separate embodiment of the invention. In some embodiments, window region 116 comprises a cross-sectional area at the surface of substrate 114 of between 10-500, 10-600, 10-700, 10-800, 10-900, 10-1000, 100-500, 100-600, 100-700, 100-800, 100-900, 100-1000, 200-500, 200-600, 200-700, 200-800, 200-900, 200-1000, 300-500, 300-600, 300-700, 300-800, 300-900, 300-1000, 400-500, 400-600, 400-700, 400-800, 400-900, 400-1000, 500-600, 500-700, 500-800, 500-900 or 500-1000 μm². Each possibility represents a separate embodiment of the invention. Optionally, the cross-sectional area of etched window region 116 tappers as it passes through substrate 114 such that the area is smaller when it reaches film 115. Window region 116 results in a free-hanging membrane 117, which is the exposed section of film 115. In some embodiments, the cross-sectional area of membrane 117 is about 20 μm². In some embodiments, the cross-sectional area of membrane 117 is at least 1, 3, 5, 10, 15, 20, 25, 30, 35, 40, 45 or 50 μm². Each possibility represents a separate embodiment of the invention. In some embodiments, the cross-sectional area of membrane 117 is at most 10, 15, 20, 25, 30, 35, 40, 45, 50, 60, 70, 80, 90 or 100 μm². Each possibility represents a separate embodiment of the invention. In some embodiments, the cross-sectional area of membrane 117 is between 1-50, 1-40, 1-30, 1-25, 1-20, 5-50, 5-40, 5-30, 5-25, 5-20, 10-50, 10-40, 10-30, 10-25, 10-20, 15-50, 15-40, 15-30, 15-25 or 15-20 μm². Each possibility represents a separate embodiment of the invention.

A nanopore 118 is formed in the membrane 117. The pore will pass completely through the membrane. Its thickness will thus equal the thickness of membrane 117. In some embodiments, the nanopore comprises a diameter not greater than 1, 2, 3, 4, 5, 10, 15, 20, 15, 30, 35, 40, 45 or 50 nm. Each possibility represents a separate embodiment of the invention. In some embodiments, the nanopore comprises a diameter not greater than 5 nm. In some embodiments, the nanopore comprises a diameter of about 5 nm. In some embodiments, the nanopore comprises a diameter between 0.5 and 10, 0.5 and 15, 0.5 and 20, 0.5 and 50, 0.5 and 75, 0.5 and 100, 1 and 10, 1 and 15, 1 and 20, 1 and 50, 1 and 75, 1 and 100, 3 and 10, 3 and 15, 3 and 20, 3 and 50, 3 and 75, 3 and 100, 5 and 10, 5 and 15, 5 and 20, 5 and 50, 5 and 75 or 5 and 100 nm. Each possibility represents a separate embodiment of the invention. In some embodiments, nanopore 118 has a diameter of between 1-100 nm. A skilled artisan will appreciate that the size of the nanopore can be modified depending on the molecule of interest. For smaller molecules, such as nucleic acids, the nanopore may be smaller. In some embodiments, the molecule of interest is a nucleic acid and the nanopore has a diameter of between 0.5-10, 0.5-5, 0.5-4, 0.5-3, 0.5-2, 0.5-1, 1-10, 1-5, 1-4, 1-3, 1-2, 2-10, 2-5, 2-4, or 2-3 nm. Each possibility represents a separate embodiment of the invention. In some embodiments, the nucleic acid is selected from RNA, single-stranded DNA (ssDNA), double-stranded DNA (dsDNA), locked nucleic acids (LNA), peptide nucleic acids (PNA), a Morpholino and a combination thereof. In some embodiments, the nucleic acid is selected from RNA, single-stranded DNA (ssDNA), double-stranded DNA (dsDNA) and a combination thereof. For larger molecules, such as proteins, the nanopore may be larger. In some embodiments, the molecule is selected from a nucleic acid, a protein, an antibody, a metabolite, a polysaccharide, and exosome and a combination thereof. In some embodiments, the molecule of interest is a protein, and the nanopore has a diameter of between 5-20, 5-15, 5-10, 4-20, 4-15, 4-10, 3-20, 3-15, 3-10, 3-5, 2-20, 2-15, 2-10, 2-7, 2-5, 2-4, or 2-3 nm. Each possibility represents a separate embodiment of the invention. In some embodiments, the molecule of interest is a protein, and the nanopore has a diameter equal to or greater than 5, 10, 15, 20, 25 or 30 nm. Each possibility represents a separate embodiment of the invention. As proteins can greatly vary in size the nanopore diameter can be further optimized to the size of the protein. In some embodiments, the protein is denatured protein. In some embodiments, the protein is non-denatured protein.

The nanopore can be generated by any method known in the art, including, but not limited to focused electron beam milling and dielectric breakdown. Nanopore 118 and dielectric membrane 117 are situated on the side of carrier substrate 114 that is in direct contact with microfluidic layer 101, so that molecules in the solution in chamber 112 have access to nanopore 118 for subsequent sensing. Microfluidic layer 101 is designed and aligned so that the nanopore is situated within chamber 112 of the channel. The microfluidic layer 101 and the nanopore layer are in fluid contact via the nanopore. In some embodiments, the film 115 is the bottom surface of the microchannel. In some embodiments, at least a part of film 115 is at least a part of the bottom surface of the microchannel. In some embodiments, the microchannel comprises at least a region of the film. In some embodiments, the nanopore is in the wall of the microchannel. In some embodiments, the nanopore is in a surface of the microchannel. In some embodiments, the nanopore is within the microchannel. In some embodiments, the nanopore is in a surface in the microchannel. In some embodiments, the nanopore is in a surface in the inside or lumen of the microchannel.

Lower reservoir 121 is on the trans side of nanopore 118. Electrode 120 is configured to contact the fluid in lower reservoir 121 so that an electrical field can be generated in the Z direction to induce translocation through the nanopore. This electrical field can be generated with a dedicated electrode for this purpose, such as electrode 111, or with either one of the focusing electrodes 107 and 110. The dimensions of lower reservoir 121 are generally immaterial to the operation of the device, but the reservoir should be of sufficient size that migration of molecules through the nanopore does not adversely affect the relative conductivity of the cis and trans sides.

In some embodiments, the device and/or system further comprises at least one detector on the trans side of the nanopore for detecting and/or measuring molecules as they pass through the nanopore. In some embodiments, the nanopore itself is the detector. In some embodiments, the nanopore is not the detector. The detection equipment required for nanopore-based single molecule detection are well known in the art. Any nanopore setup known in the art, including any detection devices, light sources, electrodes, etc. may be used and may be a part of the device and/or system of the invention. In some embodiments, the detector is configured to detect molecules at each nanopore. In some embodiments, the detector is configured to detect molecules at all nanopores. In some embodiments, multiple detectors detect molecules at multiple nanopores. In some embodiments, detecting molecules comprises detecting fluorescence. In some embodiments, the detecting is electrical detecting.

Figure 1C:
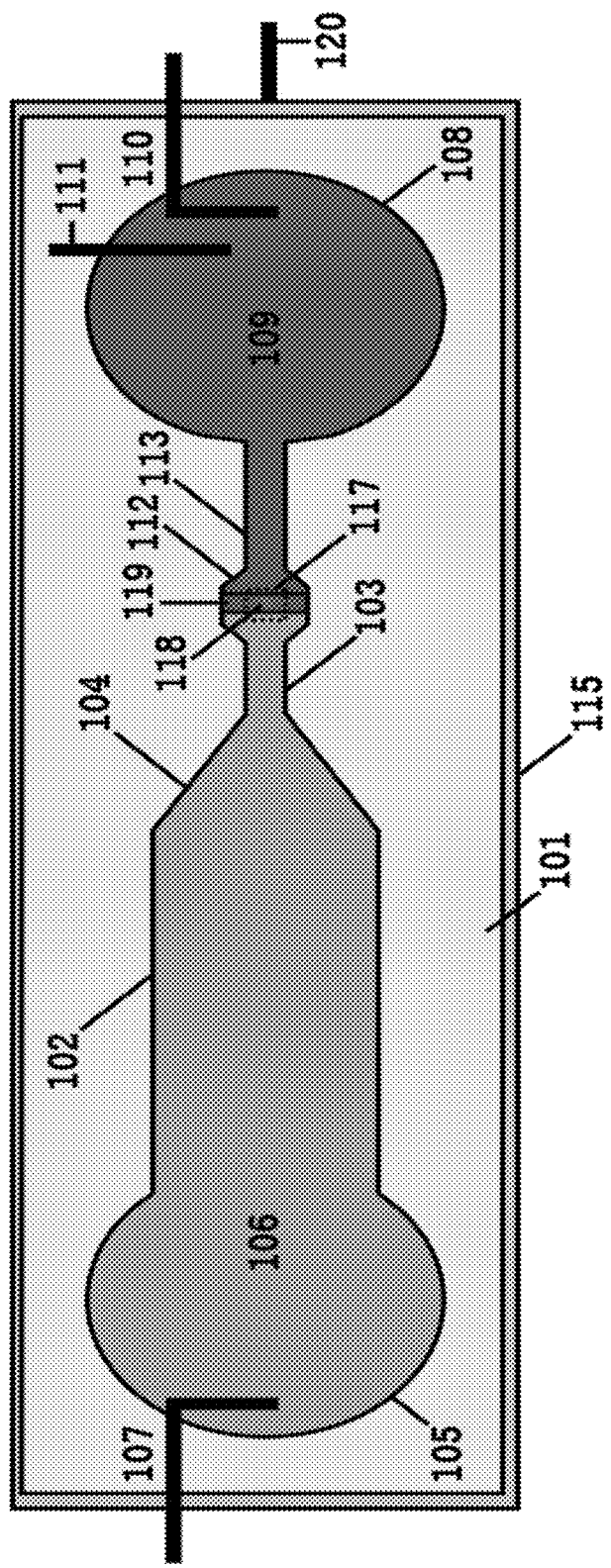

The running of the ITP and a description of the fluidics movement is now provided. Reference is made to FIG. 1C as well as 1A. FIG. 1C shows the fluidics movement during the running of ITP device, specifically to the point where the ITP sample zone 119 (the interface) is at nanopore 118. This movement can be compared to the initial fluidics setup shown in FIG. 1A.

Left reservoir 105 is initially filled with a terminating electrolyte (TE) 106. TE 106 is electrically contacted by separation cathode 107. Right reservoir 108 and the remainder of the microchannel (102, 103, 104, 112, and 113) are initially filled with leading electrolyte (LE) 109. Right reservoir 108 is electrically contacted by separation anode 110. The target analyte is initially mixed with either TE 106 or LE 109 or is injected between the TE and LE. The electrophoretic mobility of the target analyte is lower than that of the LE, but higher than that of the TE. While either the TE or LE can initially be made to contain the target analyte, the choice yielding a stronger concentration enhancement by ITP can be made based on the original source of target analytes, as well as on the mobility of the target analytes. For instance, if the target analytes are originally present in a urine sample, which is generally known to contain high concentrations of high-mobility chloride ions, the operator may choose to mix the sample with the LE or to elute the target analytes from the sample into the LE so that any remaining contaminants do not adversely affect ITP focusing. Furthermore, it has been shown that the choice of sample placement can be made given only information about the estimated electrophoretic mobility of the target analyte and the terminating and leading ions. Such decisions can be made by a person skilled in the art of ITP focusing. In some embodiments, a solution comprising the molecules of interest are added to any one of: the TE, the LE and a contact zone (interface) between the TE and LE.

When a DC voltage is applied across the channel (102, 103, 104, 112, and 113) using separation electrodes 107 and 110 a moving boundary is established between the discontinuous electrolyte system consisting of TE 106 and LE 109. Due to a gradient in the electric field at the interface between the TE and LE, target analyte ions are locally concentrated at the interface, forming an ITP sample zone 119 where the concentration is enhanced compared to the initial concentration in solution. The nanopore must be placed at a position in the microchannel such that it is a sufficient distance from the LE electrode to allow for focusing to complete, or to nearly complete by the time the interface reaches the nanopore. In some embodiments, the nanopore is at a distance from the electrodes sufficient to allow for at least 20%, 30%, 40%, 50%, 60%, 70%, 75%, 80%, 85%, 90%, 95%, 97%, or 99% of the molecules to focus in a region proximal to the nanopore. Each possibility represents a separate embodiment of the invention. The focusing is typically run with a current of 100-1000 V. The voltage will determine the rate of focusing and the rate of movement of the molecules and the positioning of the nanopore can be determined based on how long a run should be and the voltage applied.

In some embodiments, the microchannel is configured such that the nanopore is sufficiently distanced from the first and/or second electrode to allow for at least an 50×, 100×, 500×, 1000×, 5000×, 10000, 50000×, 100000×, 500000×, or 1000000× increase in concentration of the molecule of interest. Each possibility represents a separate embodiment of the invention. In some embodiments, the microchannel is configured such that the nanopore is sufficiently distanced from the first and/or second electrode to allow for at least an 100× increase in concentration of the molecule of interest. In some embodiments, the microchannel is configured such that the nanopore is sufficiently distanced from the first and/or second electrode to allow for an increase in concentration of the molecule of interest of between 100×-1000000×, 100×-500000×, 100×-100000×, 100×-50000, 100×-10000×, 100×-5000, 100×-1000×, 500×-1000000×, 500×-500000×, 500×-100000×, 500×-50000, 500×-10000, 500×-5000×, 500×-1000×, 1000×-1000000×, 1000×-500000×, 1000×-100000×, 1000×-50000×, 1000×-10000× or 1000×-5000×. Each possibility represents a separate embodiment of the invention. In some embodiments, the increase is as compared to the initial concentration of the molecule of interest. In some embodiments, the increase is as compared to a concentration of the molecule of interest when it was deposited in the device. In some embodiments, the increase is as compared to a concentration of the molecule of interest in a reservoir of the electrokinetic focusing apparatus. In some embodiments, the increase is as compared to a concentration of the molecule of interest before electrokinetic focusing. As used herein, the terms "focusing factor" and "focusing ratio" are interchangeable and refer to the increase in the concentration of the molecule of interest upon completion or termination of focusing. In some embodiments, the microchannel is configured such that the nanopore is sufficiently distanced from the first and/or second electrode to allow for a focusing factor of at least 50×, 100×, 500×, 1000×, 5000×, 10000, 50000×, 100000×, 500000×, or 1000000×. Each possibility represents a separate embodiment of the invention. In some embodiments, the focusing factor is at least 100×.

The current should be run for a time sufficient for the interface to be proximal the nanopore. In some embodiments, the current is run for a time sufficient for the focusing ratio to be at least 50×, 100×, 500×, 1000×, 5000×, 10000, 50000×, 100000×, 500000×, or 1000000×. Each possibility represents a separate embodiment of the invention. In some embodiments, the focusing factor is at least 100×. In some embodiments, the current is run for a time sufficient for the molecule of interest to be proximal to the nanopore.

In one embodiment, once the moving sample zone 119 reaches the chamber 112 where the nanopore 118 is located, the separation voltage is removed so that the focused sample zone 119 remains in the vicinity of the nanopore 118. This operation can be performed either by the operator, or by using automated feedback control based on tracking of zone 119. Zone 119 can be tracked in any way which precisely monitors its location with enough accuracy to place zone 119 within the capture region of nanopore 118. The tracking can be carried out, for instance, with a fluorescent tracer which co-focuses at the ITP interface 119 or based on a change in slope of the current-time trace, indicating that the ITP interface has entered chamber 112. In some embodiments, the device or system comprises sensors for monitoring the position of zone 119. In some embodiments, the sensors detect fluorescence. These sensors can be optical and/or electrical, so long as they can accurately monitor the position of zone 119 relative to nanopore 118.

In some embodiments, the sensor detects a position of the molecule of interest from the analyte in the microchannel. In some embodiments, the sensor directly detects the molecule of interest or a moiety attached thereto. In some embodiments, the sensor detects changes in the fluid in the microchannel. In some embodiments, the detection is optical detection or electrical detection. In some embodiments, detecting a position of the molecule comprises optically detecting changes in the fluid in the microchannel. In some embodiments, optically detecting comprises detecting at least one of a marker or tracer in the fluid, and an optical property of the fluid. For example, a change in the fluid could be a change in the position of the dye or tracer. If the dye is in the LE for instance as the LE migrates the dye would also migrate which could be detected optically. Similarly a tracer that travels in the interface (though not connected to the molecule of interest) could be monitored optically for changes in the position of the interface. In some embodiments, the marker is a fluorochrome or a dye. In some embodiments, the optical property is selected from absorbance of the fluid, refraction of the fluid and interference of the fluid. In some embodiments, detecting a position of the molecule comprises electrical detection of a change in the microchannel. In some embodiments, detecting a position of the molecule comprises detecting an electrical change in the fluid in the microchannel. In some embodiments, said electrical change comprises change in at least one of voltage, current, resistance, conductivity and impedance. In some embodiments, detecting electrical change in the microchannel comprises detecting the change in the rate of current decrease as the interface passes through a tapered section of the microchannel.

In some embodiments, the sensor is one of the electrodes. In some embodiments, the sensor is not one of the electrodes. In some embodiments, the sensor is a nanopore. In some embodiments, the sensor is not a nanopore. In some embodiments, the sensor detects when the molecule or interface is proximal to the nanopore. In some embodiments, the sensor detects the position of the molecule or interface in the microchannel and extrapolates when the molecule or interface will be proximal to the nanopore. In some embodiments, the sensor controls the running of current for focusing. In some embodiments, the sensor controls the running of current for translocation through the nanopore. In some embodiments, the device further comprises a control unit. In some embodiments, the control unit control the focusing current, the translocation current or both. In some embodiments, the control unit is connected to the sensor in order to time switching from focusing to translocation.

The term "moiety", as used herein, relates to a part of a molecule that may include either whole functional groups or parts of functional groups as substructures. The term "moiety" further means part of a molecule that exhibits a particular set of chemical and/or pharmacologic characteristics which are similar to the corresponding molecule. In some embodiments, the moiety is a fluorochrome.

In some embodiments, the separation voltage may be maintained when ITP interface 119 reaches nanopore 118, and bulk flow may be induced (e.g. by applying electroosmotic or hydrodynamic flow) opposite to the direction of ITP migration to balance the migration of target analyte ions. In some embodiments, chamber 112 is closed off such that the voltage no longer reaches the desired molecules and thus is immaterial. In some embodiments, the device further comprises a capturing element. In some embodiments, the capture element is proximal to the nanopore. In some embodiments, the capture element is within the capture region of the nanopore. In some embodiments, the capture element is configured to capture the molecule of interest in a region of the microchannel proximal to the nanopore. In some embodiments, capturing comprises closing off a region of the microchannel in some embodiments, the region is a region proximal to the nanopore. In some embodiments, the region is the region of the interface. In some embodiments, the closing element is at least one valve. In some embodiments, the closing element is a plurality of valves. In some embodiments, the capture element comprises at least 2 valves proximal to the nanopore. In some embodiments, the valve is configured to enclose fluid in the microchannel proximal to the nanopore.

In some embodiments, the capture element comprises an element that binds to the molecule of interest or a moiety attached thereto. In some embodiments, the capture element comprises antibodies to the molecule of interest. Any binding agent specific to the molecule of interest may be employed. For example, compounds known to specifically bind nucleic acids may be used to capture nucleic acids to be analyzed. In some embodiments, the capture element binds a moiety attached to the molecule of interest. As a non-limiting example, the molecule of interest may by biotin labeled and the capture element may be streptavidin coated. Other capture combinations, such as FLAG-tag and FLAG beads, or MYC-tag and MYC binding protein (MYCBP) to name just two, can also be employed.

In some embodiments, the capturing element is configured to be cleaved. In some embodiments, the capturing element is cleavable. In some embodiments, the moiety attached to the molecule is configured to be cleaved or is cleavable. It will be understood by one skilled in the art that after capture of the molecule proximal to the nanopore there must be release of the molecule so that it can translocate through the nanopore. In embodiments, wherein the area proximal to the nanopore is enclosed but the molecule of interest is not bound, release and/or cleavage is not necessary. Cleavable molecules are well known in the art and include photocleavable and chemically cleavable options. In some embodiments, the capture element and/or moiety is photocleavable.

With sample zone 119 (and the molecule of interest) now stationary over nanopore 118, a translocation voltage is applied between translocation electrodes 111, 120. Electrode 111 is optional, and electrode 107 or 110 may be used for translocation. In the case where the target analyte is an anion, the translocation electrode on the cis side 111 of the nanopore is the cathode, whereas the translocation electrode on the trans side 120 of the nanopore is the anode. Given that a high ionic conductivity is required on the cis side of the nanopore to achieve a high fractional current blockade and given that the ionic conductivity of the LE is typically higher than that of the TE, the cis-side translocation electrode 111 may preferably contact the LE, either directly from LE reservoir 108 or from inside channel section 113 containing LE, though this is not required. On the trans side, electrode 120 electrically contacts the nanopore 118 through an electrolyte solution in reservoir 121.

When a translocation voltage is applied, the translocation of anions through nanopore 118 leads to a drop in the background current caused by translocation of abundant background cations in the opposite direction. This current blockage by anions as a function of time is a signature of the translocating anion and is recorded on a computer as evidence of the presence of a particular target analyte. In other embodiments, optical sensing may be used as a detection method instead of electrical sensing. For instance, for a nucleic acid target, specific sequences can be pre-hybridized with fluorescently labeled probes in multiple colors which are probed upon translocation of the target through the nanopore and can be imaged with high sensitivity optical microscopy apparatus. The use of such methods does not affect the functioning of the invention and are considered standard practice for those skilled in the art. Indeed, any nanopore setup with any detection method known in the art may be used as part of the device and/or system of the invention.

While the aforementioned is generally relevant to the target analyte being an anion, the functionality of the invention is not affected if the target ion is a cation. In this case, the qualitative mobility constraints for the LE and TE remain unchanged, but the electrolyte system used for ITP must contain leading and trailing cations (as opposed to anions). The polarity of separation electrodes 107, 110 must also be reversed. For detectable translocation of cations focused using ITP, the translocation electrolyte in reservoir 121 must provide a baseline current of anions through the nanopore, and the polarity of the translocation electrodes 111, 120 must be reversed.

Buffer Compatibility

As previously mentioned, it is technically problematic for the nanopore buffer and ITP buffer to be compatible. In order to focus a target analyte using ITP, the electrophoretic mobility of the analyte must be bracketed by that of the dominant ion in the TE and LE, i.e. the mobility of the terminating and leading ions must respectively be smaller and larger than that of the analyte. A typical range of the electrophoretic mobility of DNA is ~20-40×10$^{-9}$ m$^2$V$^{-1}$s$^{-1}$ (largely independent of the length). Examples of electrolytes used for focusing DNA using anionic ITP are a LE buffer consisting of 200 mM tris and 100 mM HCl ($\mu_L$=−68×10$^{-9}$ m$^2$V$^{-1}$s$^{-1}$, $\sigma_L$=0.87 S/m).

While an electrolyte conductivity of <1 S/m on the cis side of the nanopore is sufficient for ITP focusing, translocation signal amplitude is proportional to conductivity, and a higher conductivity is required for the baseline current to be above the system noise floor (for detectable translocation, buffer conductivities above 1 S/m are preferred). A common electrolyte composition on the cis side of the nanopore is therefore 40 mM tris, 1 mM EDTA and 1 M KCl, having a conductivity of 15 S/m. In practice, 100-200 mM is the lower limit of the KCl concentration, as lower concentrations lead to a current increase upon analyte translocation, which complicates the detection of translocation events. It is primarily the LE that is located proximal to the nanopore, and a high ionic strength in the LE is known to reduce the electrophoretic mobility of analytes, thus adversely affecting the focusing of analytes into the sample zone. Experiments were run to find a LE composition that would work for translocation through the nanopore, and also for ITP focusing. The results are summarized in Table 1.

TABLE 1

LE Buffer composition

| Composition of leading electrolyte (LE) | Qualitative focusing performance |
| --- | --- |
| 100 mM tris, 50 mM KCl, 50 mM HCl | +++ |
| 200 mM tris, 100 mM KCl, 100 mM HCl | +++ |
| 200 mM tris, 200 mM KCl, 100 mM HCl | +++ |
| 300 mM tris, 150 mM KCl, 150 mM HCl | +++ |
| 200 mM tris, 500 mM KCl, 100 mM HCl | ++ |
| 200 mM tris, 600 mM KCl, 100 mM HCl | + |
| 200 mM tris, 600 mM KCl, 100 mM HCl, 1% m/v PVP | ++ |
| 200 mM tris, 700 mM KCl, 100 mM HCl | + |
| 200 mM tris, 800 mM KCl, 100 mM HCl | − |
| 200 mM tris, 1000 mM KCl, 100 mM HCl | − |

As no voltage will be applied over the TE during translocation, its composition is less critical for successful translocation than that of the LE. A typical TE buffer suitable for ITP focusing consists of 20 mM tris and 10 mM tricine ($\mu_T$=−18×10$^{-9}$ m$^2$V$^{-1}$s$^{-1}$, $\sigma_T$=0.035 S/m). This is the TE buffer used in the experiments summarized in Table 1. It is important however, that the TE does not contain any components that may adversely affect translocation of analyte ions through the nanopore, such as large molecules which may block the pore, or small molecules that may translocate or interfere with detection by contributing to the background signal.

The experiments showed that good ITP focusing was achieved with a LE comprising anywhere from 50 to 500 mM KCl. Other monovalent strong base cations (such as Na+ and Li+ for example) could be used in place of K+. A LE comprising 200 mM tris, 100 mM HCl was also found to be optimal. Focusing deteriorating at KCl concentrations above 700 mM and even at 700 mM itself the focusing was poor. Interestingly, addition of polyvinylpyrrolidone (PVP) to the LE improved focusing at higher KCl concentrations.

In order for there to be proper operation of the nanopore the strong cation concentration on the trans side of the nanopore must be considered. The concentration of the strong cation on the trans side must be equal to, or greater, than the concentration on the cis side. Thus, for a LE buffers with 100 mM KCL the trans side must have a concentration of at least 100 mM. In some embodiments, the concentration on the trans side is at least 1.25, 1.5, 1.75, 2, 2.5, 3, 3.5, 4, 4.5, 5, 6, 7, 8, 9, or 10 times the concentration on the cis side. Each possibility represents a separate embodiment of the invention. In particular for low concentrations on the cis side, higher concentration on the trans side may be beneficial. The concentration on the trans side may be above 1M. In some embodiments, the concentration on the trans side is at least 50, 100, 150, 200, 300, 400, 500, 1000, 1500, 2000, 2500, 3000, 3500, 4000, 4500, or 5000 mM. Each possibility represents a separate embodiment of the invention.

Nanopore-Compatible Electroosmotic Flow Suppression

When a voltage is applied to such a buffer system, an electroosmotic flow (EOF) will be established in the direction opposing the movement of the ITP interface. As the electroomostic mobility is on the same order of magnitude as the electrophoretic mobility of the target ions ($\mu EO \approx 30 \times 10-9$ m2V−1s−1), this EOF 'counter-flow' disrupts the ITP focusing by dispersing the interface, effectively reducing the local concentration of target analytes. This effect can be overcome by adding large polymer molecules such as polyvinylpyrrolidone (PVP) to the LE to reduce the electroosmotic mobility. Alternatively, static surface coatings such as grafted Poly(oxyethylene) layers or adsorbed triblock copolymer compounds such as Pluronic may be used to achieve the same effect. An important consideration in choosing a polymer for surface coating is that the molecule should not block the nanopore for translocations of the target analyte. For this reason, the coating with polymers may be performed before the running of the apparatus.

Coating agents to reduce EOF are known in the art. Examples of coating include Si-POE and POE triblock copolymers. These can be easily adhered to PDMS surfaces and the like. There are also solution-deposited options, that while in solution coat surface. Such options should ideally be used before running of the apparatus so that free polymers in the solution do not block the nanopore. Optionally, the nanopore may be covered or absent during coating so that the nanopore does not become clogged or obscured. Non-limiting examples of solution-deposited options include PVP and (3-Aminopropyl)trimethoxysilane (APTMS). The effects of these and other molecules on EOF are known. While the short-chain Si-POE is similar to APTMS and is therefore likely to work for nanopores, longer-chain Si-POE-Si reduces EOF by 75%. The reduction is better, 86%, for the Pluronic (Poly(ethylene glycol)-block-poly(propylene glycol)-block-poly(ethylene glycol)) F108 on native PDMS surfaces. However, the long F108 molecules are a risk for clogging the nanopore. The molecular weight (MW) of APTMS is ~180. The MW of the shortest Si-POE is ~500. The MW of Pluronic is ~14,000. Thus, all of these molecules have advantages and drawbacks for use in the device of the invention. They are thus tested for their effect on EOF in the invention. A PDMS/glass ITP apparatus is tested, either with no coating, coating with APTMS or coating with Pluronic. For APTMS the reservoirs are filled with 150 uL of 0.5M TBACl in anhydrous MeOH, with a spike in of 5 uL 95% APTMS. For Pluronic the device is filled with a 3 uM solution in 10 mM phosphate buffer (pH 8.2) for 20 h; washed in DI and dried with $N_2$. The Pluronic, similar to PVP effects a good reduction in EOF, producing a superior focusing as compared to the uncoated device. This is especially true at higher concentrations of KCl in the LE buffer.

It was then tested whether the surface coatings inhibited nanopore translocation. Preliminary nanopore experiments showed that uninhibited translocations still occurred in the presence of 0.5% w/v PVP in the LE, and after soaking the channel in a solution of Pluronic F127 (15 μM in phosphate buffer, pH 8.0) for 20 hours. Pluronic was not added to the LE, but rather used to treat the device first before running the nanopore. Thus, the surfaces of the device can be coated with Pluronic, allowed to rest (optionally 24 hours) and then used for the methods of the invention. Additionally, PVP may be added to the LE, TE or both.

As the ITP velocity decreases as the interface migrates through the microchannel, the forward ITP velocity may at some point be balanced by EOF counter-flow if EOF is not entirely suppressed. In one embodiment of the invention, EOF control would be suppressed such that the interface travels unimpeded. This is desirable as concentration increases proportional to the distance the interface travels. In an alternative embodiment of the invention, the velocity of the ITP interface may be balanced by the velocity of the EOF counter-flow at the location of the nanopore in the channel, so that the molecules of interest are continuously focused into the ITP interface in proximity to the nanopore. This may be achieved, for instance, by adjusting the electroosmotic mobility to a known value through the use of surface coatings, so that the location at which forward ITP migration is balanced by counter-flow EOF may be calculated or simulated. In some embodiments, the LE comprises a composition that modulates EOF counter-flow. In some embodiments, the LE comprises a composition that reduces EOF counter-flow. In some embodiments, at least one surface of the electrokinetic focusing apparatus is coated with a composition that modulates EOF counter-flow. In some embodiments, at least one surface of the electrokinetic focusing apparatus is coated with a composition that reduces EOF counter-flow. In some embodiments, the composition comprises a polymer. In some embodiments, the composition comprises a triblock copolymer. In some embodiments, the composition comprises at least one of PVP, Pluronic, and APTMS. In some embodiments, the composition comprises PVP. In some embodiments, the composition comprises Pluronic. In some embodiments, the composition comprises at least one of PVP and Pluronic.

Figure 2A:
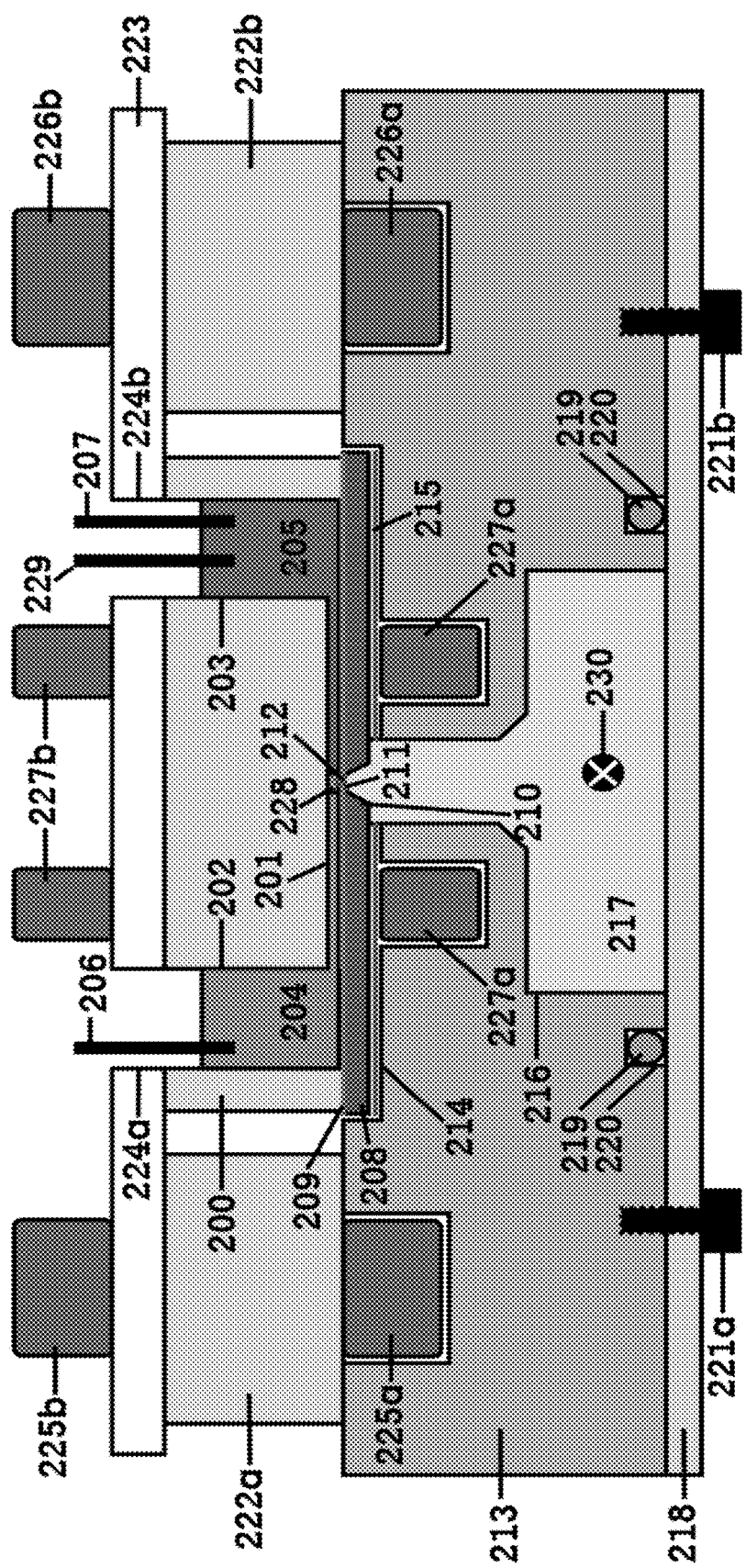
FIGS. 2A-C: (2A) A schematic side view cross-section of an embodiment of the device/system of the invention the device, wherein the microfluidics layer and nanopore layer are clamped together by a magnetic clamp setup. (2B) A schematic top view of the device/system of 2A. (2C) Photograph of a device with the schematic layout of 2A-B.

Reference is now made to FIG. 2A. FIG. 2A shows one possible embodiment of the invention. It will be understood that each new aspect introduced in FIGS. 2A-C, can be added individually to the device/system described in FIGS. 1A-C, and that they need not all be added. The device in FIG. 2A comprises a microfluidic layer 200. Layer 200 can be made of polydimethylsiloxane (PDMS). In layer 200 a microchannel 201 is patterned, optionally using soft lithography. Two reservoirs 202 and 203 are punched through the full thickness of the layer, to provide external access to microchannel 201. During running the left reservoir 202 is filled with a mixture of TE 204 and optionally target analyte and electrically contacted by a separation cathode 206. Optionally the cathode is a platinum cathode. Right reservoir 203 is filled with LE 205 and electrically contacted by a separation anode 207, which is optionally platinum. LE 205 may optionally comprise 200 mM tris, 100 mM HCl, 600 mM KCl and 0.5% m/v PVP to suppress EOF, and TE 204 may optionally comprise 20 mM tris and 10 mM tricine.

The device further comprises a nanopore layer, consisting of a carrier substrate 208. In some embodiments, the carrier is silicon. In some embodiments, the carrier is a silicon wafer. Carrier substrate 208 is coated on one side with a thin film 209. In some embodiments, film 209 is made of silicon nitride. In some embodiments, film 209 comprises a thickness of about 25 nm. On the trans side of carrier substrate 208, which is the side facing away from microfluidic layer 200, an etched window region 210 provides access to thin film 209 and forms a free-hanging membrane 211. In some embodiments, membrane 211 comprises a cross-sectional area of about 20 $\mu m^2$. At least one nanopore 212 is formed in membrane 211, optionally by controlled dielectric breakdown of nitride membrane 211, or by other methods known in the art.

The microfluidic layer 200 and nanopore device layer 208 are reversibly sealed together using a chip holder 213. As used herein, the nanopore device may also be referred to as a chip, or nanopore chip. The chip holder should be constructed of chemically inert and non-conducting materials.

In some embodiments, the chip holder is made of Teflon. Nanopore device 208 lies within a depression 214 in chip holder 213. The depth of depression 214 being substantially equal to the thickness of the chip to ensure correct alignment. Should the depth of depression 214 be greater than the thickness of the chip, an insert to go below the chip and raise it up such that it is at the top of the chip may be employed. A gasket 215 provides a leak-proof seal for nanopore device 208 against holder 213. Gasket 215 may be made of PDMS, or any other plastic or other material that is water-proof and provided a tight, leak-proof seal. In some embodiments, gasket 215 is replaced with a fast-curing polymer 'glue' or another adhesive that also provides a water-proof, tight, leak-proof seal. Chip holder 213 provides access to the bottom (trans side) of nanopore device 208 through a translocation chamber 216. During running of the device chamber 216 is filled with a translocation electrolyte 217. Translocation chamber 216 is closed with a lid 218. Lid 218 may be made of Plexiglas or another strong, water-proof polymer or composition suitable for the purpose of closing chamber 216. Optionally, an O-ring 219 in a trench 220 provides a leak-proof seal. O-ring 219 and trench 220 may face the surface of holder 213 and contact lid 218. Lid 218 is held in place by at least two screws 221*a*, 221*b*. The number of screws will be sufficient to hold lid 218 in place without any leakage of electrolyte 217.

On the microfluidic side of the device, two optional spacers 222*a* and 222*b* on either side of microfluidic layer 200 support an optional top plate 223 with holes 224*a* and 224*a* which provide access to microfluidic reservoirs 202, and 203. Top plate 223 may be made of PDMS or other polymers such that it provides a stable and resilient top to the device. Top plate 223 may optionally be adhered or attached to spacers 222, microfluidics layer 200 or both. Holes 224*a* and 224*b* may be formed in top plate 223 by any method known in the art, including, but not limited to, mechanical drilling, laser cutting, and sand-blasting. In alternative embodiments, spacers 222*a* and 222*b* may be connected to microfluidic layer 200.

The assembly of chip holder 213, nanopore device layer 208, microfluidic layer 200, spacers 222 and top plate 223 is held together by at least one pair of magnets, selected from the three pairs of magnets 225, 226 and 227. Two pairs of disc magnets 225 and 226 exert a vertical force on spacers 222. Magnets 225*a* and 226*a* will be embedded in holder 213. Magnets 225*a* and 226*a* may be adhered to or attached to holder 213. Magnets 225*a* and 226*a* will be positioned in holder 213, such that when microfluids layer 200 is properly aligned on top of nanopore layer 208 (that is with membrane 211 flush against the bottom of the microfluidics and aligned with a hole in channel 201 such that fluid in channel 201 can contact nanopore 212) the magnets are directly below spacers 222. Magnets 225*b* and 226*b* will thus be on top of optional top plate 223, or on top of spacers 222. This arrangement magnetically holds microfluidic layer 200 flush and aligned with nanopore device layer 208. In some embodiments, the device comprises two pairs of magnets 225 and 226. In some embodiments, the device comprises one pair of magnets 225 or 226. Further, an optional vertical clamping force in the center of the assembly is provided by a pair of ring magnets 227*a*, and 227*b*. There may be two magnets 227*a* imbedded in chip holder 213 or only one magnet 227*a*. Correspondingly there may be one or two magnets 227*b* above the central region (between holes 224*a* and 224*b*) of top plate 223. Magnets 227*a* and 227*b* will be aligned so that when the force is applied it properly aligns and holds in place microfluidics layer 200 and nanopore layer 208. Top plate 223 may be made of glass, plastic or other inelastic materials that provide sufficient rigidity to distribute the clamping force exerted by the three pairs of magnets 225, 226 and 227. It shall be recognized by those skilled in the art that the sealing of microfluidic layer 200 to nanopore device 208 is not limited to magnetic clamping. Rather, holder 213 may be used, mutatis mutandis, in conjunction with other sealing or bonding methods such as clamps, locks, bolts and others.

When the target analyte 228 focused by ITP reaches the location in the microchannel 201 at which the nanopore 212 is located, the separation voltage may be removed from separation cathode 206 and separation anode 207, and a translocation voltage is applied between the translocation cathode 229 and the translocation anode 230. Translocation cathode 229 may be a separate cathode or it may be separation cathode 206. In the translocation voltage is removed, the same cathode may be used for both purposes. In some embodiment, the separation voltage is provided by a Keithley 2410 Source Meter high voltage power supply, and the translocation voltage is provided by an Agilent E3620A amplifier, but other suitable sources may be used, as identified by those skilled in the art given the aforementioned requirements. During translocation, the current read by the translocation voltage source is optionally recorded on a computer.

Figure 2B:
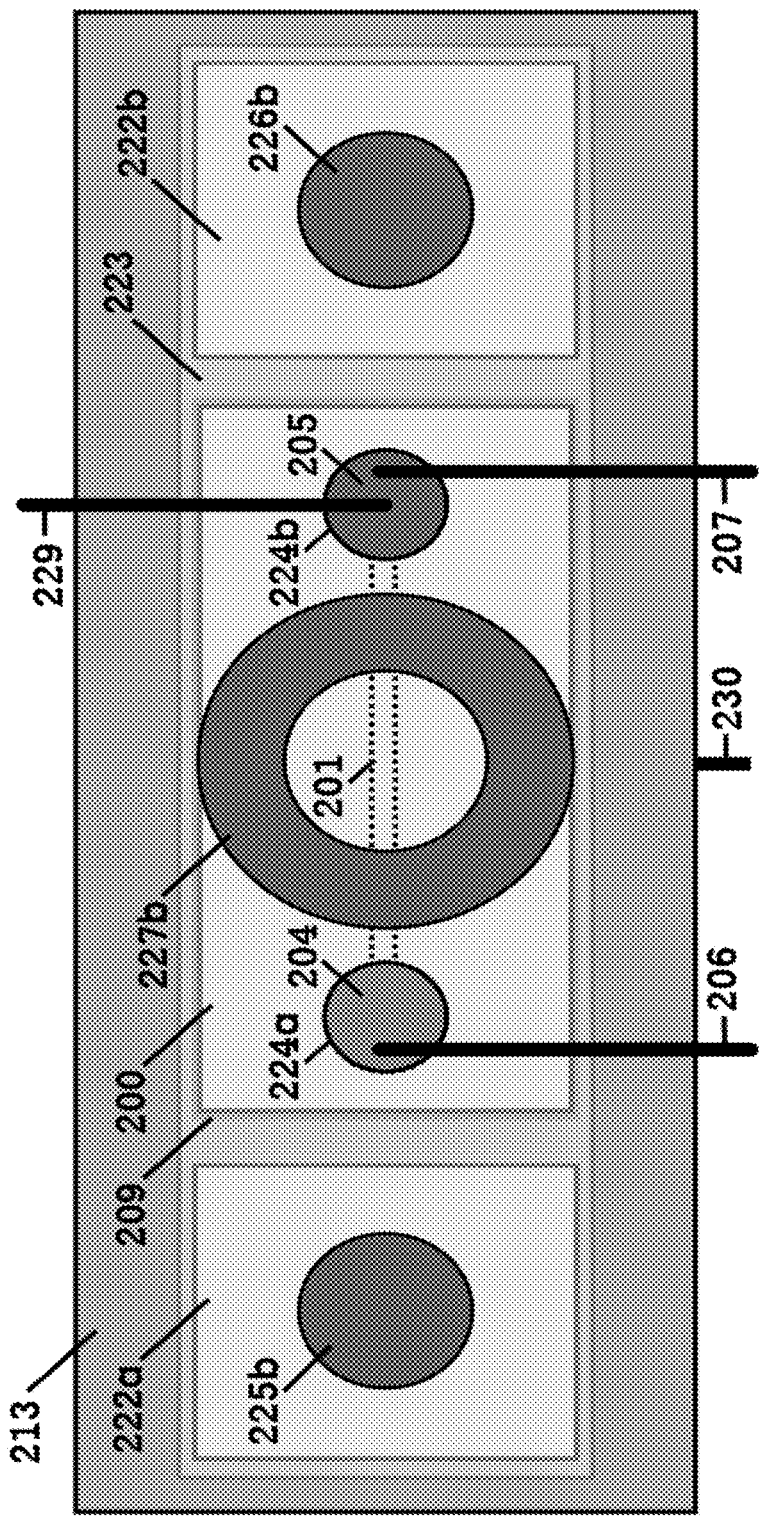

Reference is now made to FIG. 2B. FIG. 2B provides a view of the top of the device exemplified in FIG. 2A. Ring magnet 227 may be a round magnet with space in the middle such that magnet 227*a* can surround region 210. Magnets 227*b* would be of a corresponding shape. Alternatively, two magnets 227*a* could flank region 210 in place of a ring. In the aerial view, it is clear that top plate 223 is contiguous and that hole 224 pass through it but do not extend to the edge. Electrodes 206, 207 and 229 extend from the reservoirs to a power source, or optionally more than one power source. Electrode 229 need not be positioned as shown, but rather could also be in reservoir 204, or could enter channel 201 from a side. In an embodiment where electrode 229 was in channel 201 it would need to be sealed properly such that there was no leakage.

Figure 2C:
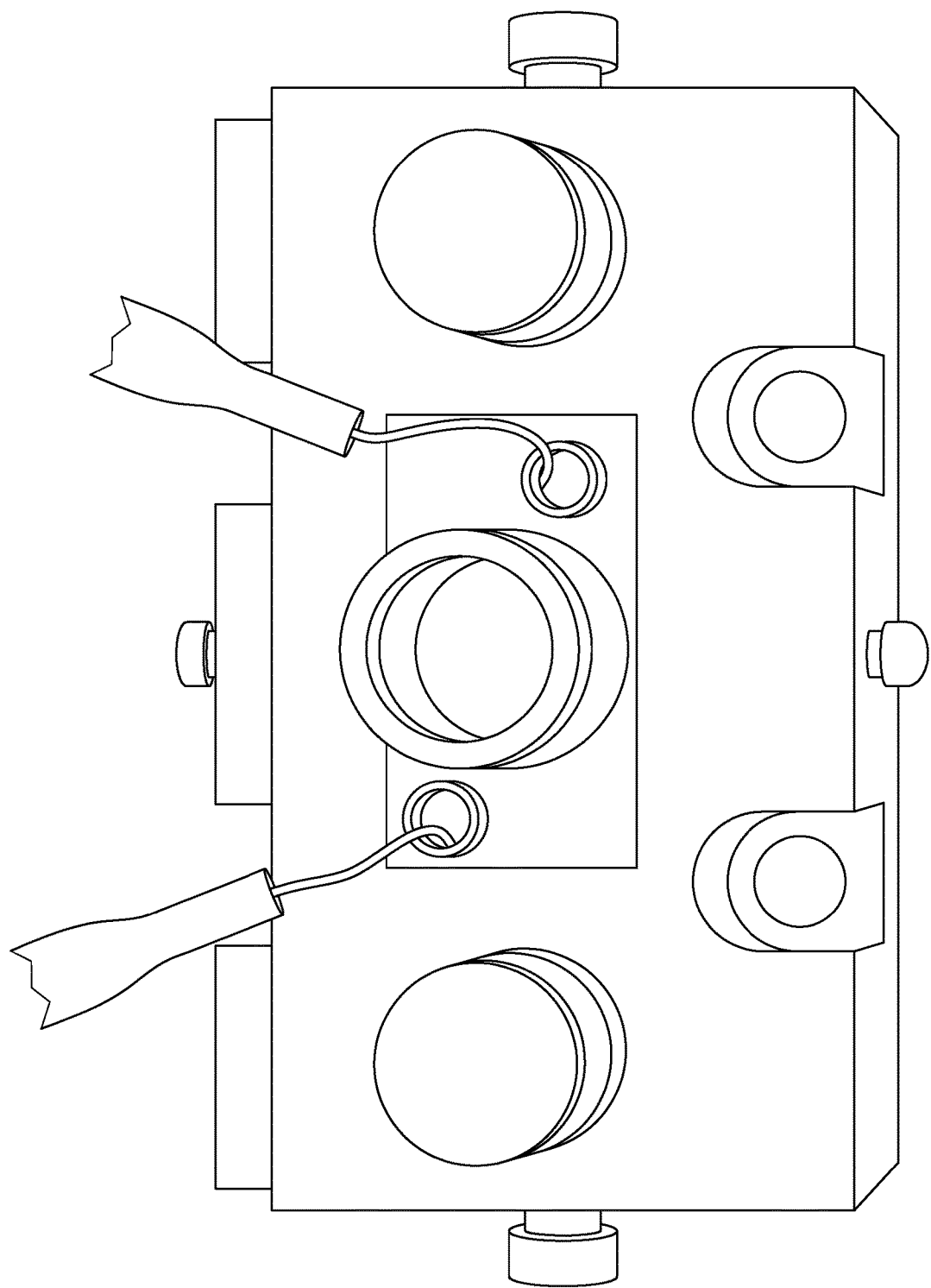

FIG. 2C is a photograph providing an aerial view, similar to 2B, of a fully functional device of the invention. The separation electrodes can be seen in this picture, though the translocation electrodes are not shown.

Figure 3A:
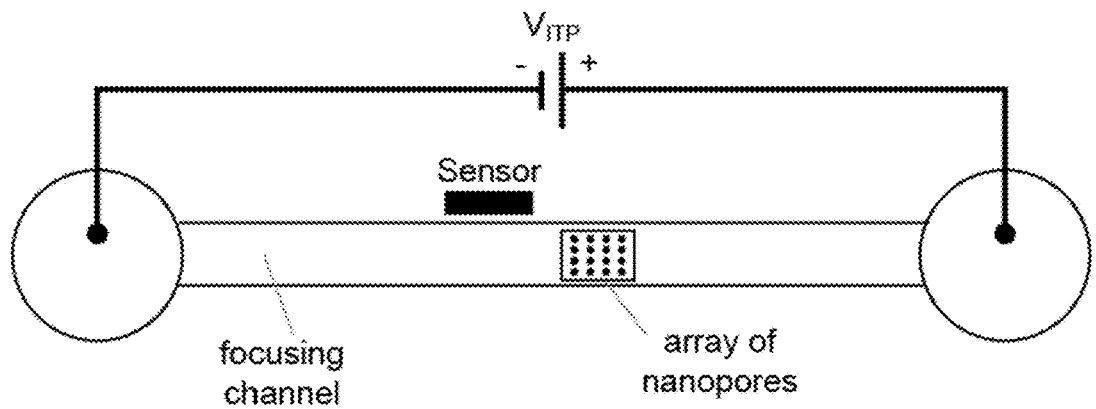
FIGS. 3A-C: A schematic top view of the device/system with a (3A) vertical format, a (3B) planar format and a (3C) curved planar format.
Figure 3B:
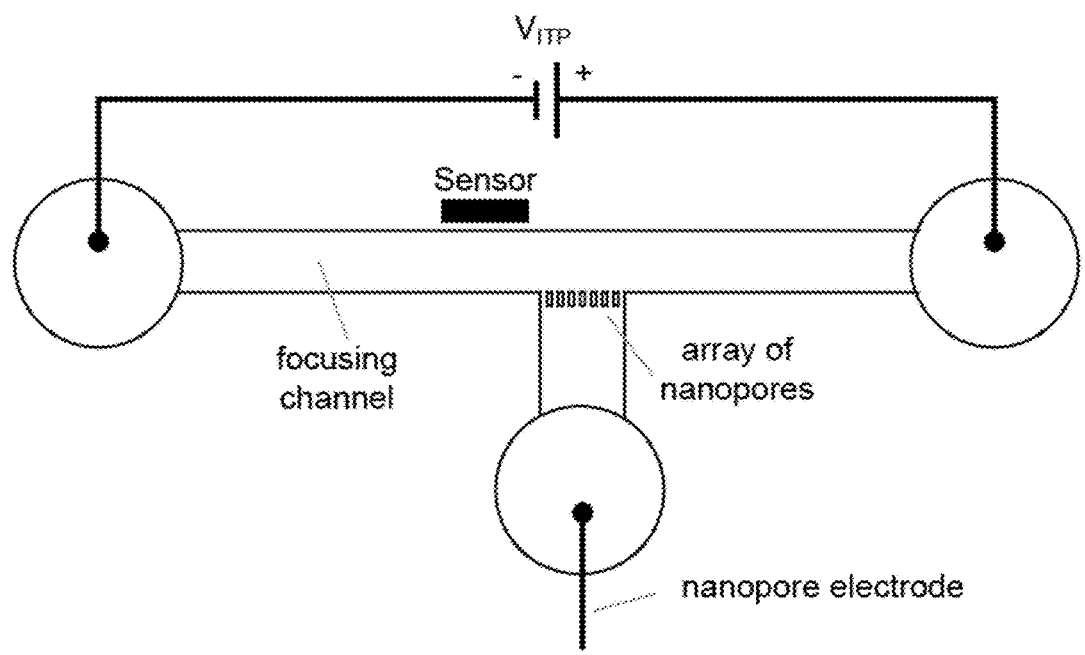

Reference is now made to FIG. 3 which provides overhead views of three embodiments of the device. FIG. 3A shows the device of the invention in a vertical format similar to how it was depicted in FIGS. 1 and 2. In this format the nanopore layer (not visible except for the nanopore array) is below the ITP layer. Such an arrangement, exemplified herein, is not mandatory. The special relationship between the two layers is irrelevant as it is an electrical current that induces translocation through the nanopore and gravity is not required. Thus, the nanopore layer may be below, above or next to the microfluidic layer. FIG. 3B shows one such embodiments, wherein the two layers are in a planar format. In both figures, the ITP electrodes are shown. The translocation electrode in the trans reservoir is also shown in FIG. 3B.

A sensor, that detects a position of a molecule of interest in the microchannel is also shown. Such a sensor is an optional feature in all embodiments of the device of the invention, even though it is not depicted in FIGS. 1 and 2. In some embodiments, the sensor is one of the electrodes. In some embodiments, the sensor is one of the focusing electrodes. In some embodiments, the sensor is not one of the electrodes. In some embodiments, the sensor is not one of the focusing electrodes. In some embodiments, the sensor is the nanopore. In some embodiments, the sensor is not the nanopore. Also, instead of a sensor a capture element is also possible, however, in such embodiments the capture element would need to be proximal to the nanopores. A sensor need not be proximal to the nanopores and indeed need not detect within the area proximal to the nanopore, rather it could detect the molecules at a point distal to the nanopore and then it would be extrapolated as to when the molecules would reach the nanopore. As described herein above, electrokinetic focusing runs have a high level of variation and the sensor allows for determining when the interface will be proximal to the nanopore. The sensor should thus detect the molecules of interest at a point after focusing has begun. Once focusing has begun, the time it will take for the focus to reach a given point can be extrapolated mathematically. Before the focusing has started the variation cannot be predicting. This is because once focusing starts it will progress at a known rate. In some embodiments, the sensor detects a position of a molecule in the microchannel after electrokinetic focusing has started. In some embodiments, the detecting is after at least 5, 10, 15, 20, 25, 30, 40, 50, 60, 70, 75, 80, 90 or 95% of the focusing has occurred. Each possibility represents a separate embodiment of the invention.

Figure 3C:
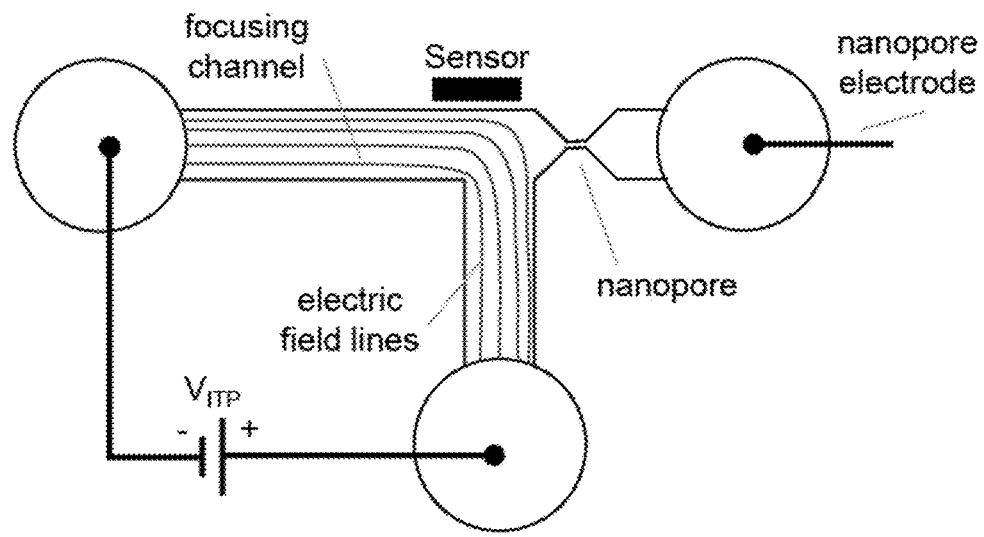

Reference is now made to FIG. 3C. FIG. 3C also shows a planar arrangement, although this is for simplicity as the embodiment is also possible with the nanopore in a vertical format (above or below the microfluidics layer). In this embodiment, the microchannel curves. In some embodiments, the microchannel comprises at least one curve. The curving results in a curved electrical field (as shown by light grey lines). In some embodiments, the nanopore is located in the curved region of the microchannel, such that it is not directly in, or contacted by, the electrical field. In some embodiments, the nanopore is in the elbow region of the curve. The distance from the nanopore to the electrical field should not be greater than the capture region of the nanopore. This configuration protects the nanopore from possible damage caused by the focusing current.

Reference is now made to FIG. 4. FIG. 4 provides overhead views of embodiments of the invention that provide an alternate configuration for protection of the nanopore during focusing. These embodiments show configurations of the device that protect the film and nanopore from damage from the focusing current by short-circuiting the nanopore. The focusing current can erode the nanopore over time and at high voltages such as might be run during focusing. To eliminate this problem the film and nanopore can be short-circuited. That is an electrical connection can be made from the microchannel or one of the microfluidic reservoirs to the trans nanopore reservoir. In this way electricity can pass from the fluidics layer to the nanopore layer without having to pass through the nanopore and damage it.

Figure 4A:
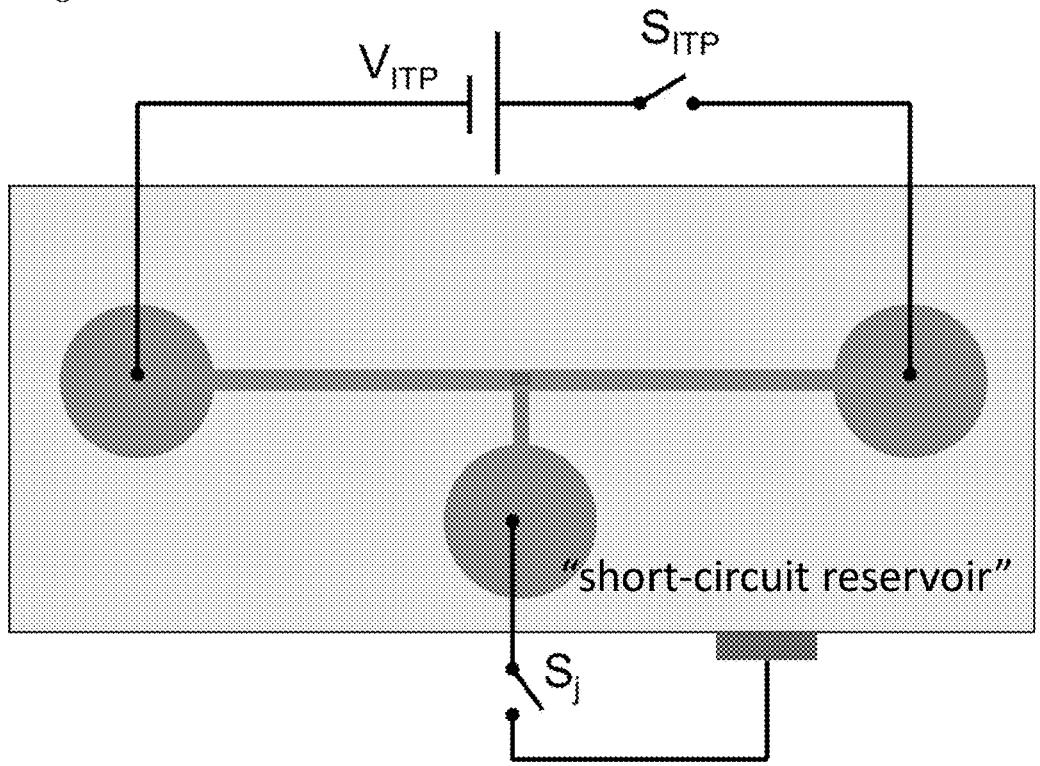
FIGS. 4A-D: A schematic top view of the device/system with the nanopore short-circuited. (4A-B) The device (4A) without and (4B) with a power source in the short-circuiting pathway is shown. (4C-D) The device with a translocating power source separate from the short-circuiting pathway running in (4C) focusing mode and (4D) translocating mode is shown.

In FIG. 4A one possible embodiment is shown comprising a third reservoir in the microfluidic layer, the "short-circuit reservoir" The third reservoir is in fluidic connection to the microchannel. In some embodiments, the connection is through a second microchannel. Neither the second microchannel nor the third reservoir are essential, rather there must be an electrical connection from the microfluidics to the trans nanopore reservoir that is not via the nanopore. This connection may have a switch (shown as $S_j$, for junction-switch) so that the electrical connection can be broken during translocation of molecules through the nanopore. The short circuit/junction microchannel and/or reservoir are depicted as extending away from the nanopore region but in fact may contact the fluidics layer at any point, optionally at any point of the first microchannel. The dark grey box at the bottom of the electrical connection from the junction switch represents the trans nanopore reservoir. The reservoir need not actually extend out to the side, but rather is so depicted here for ease of understanding.

Figure 4B:
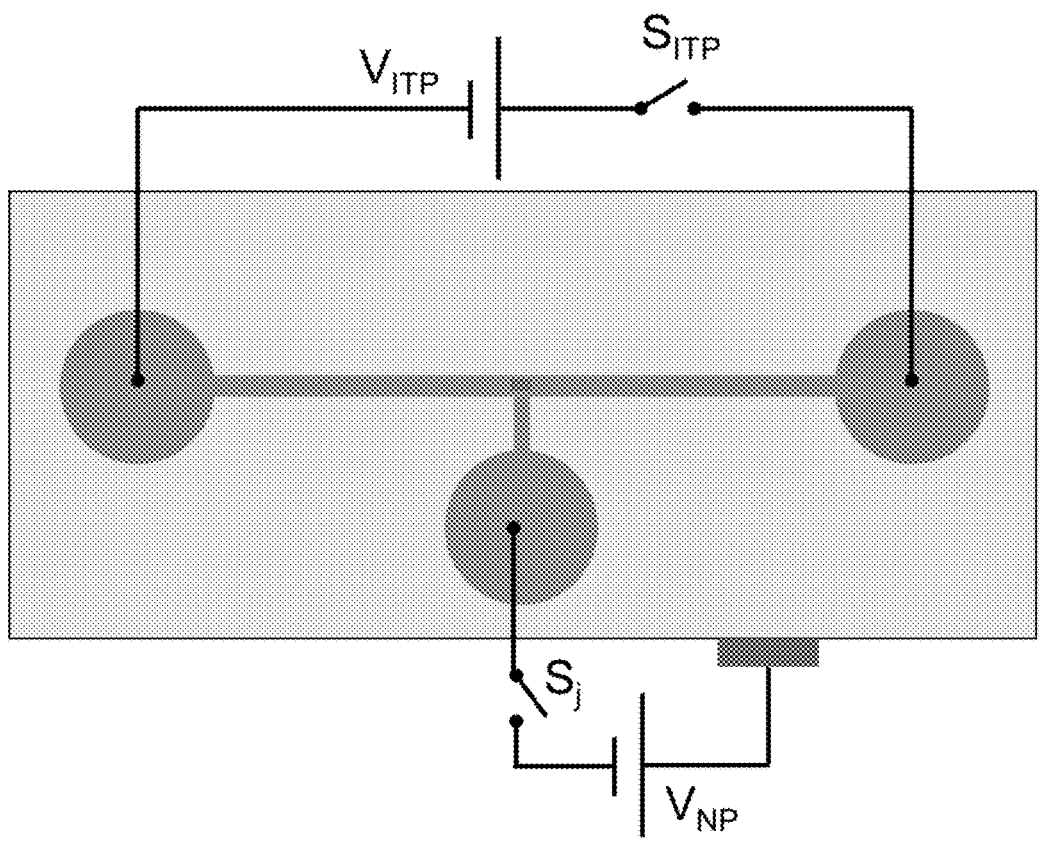

In FIG. 4B an embodiment similar to that of 4A is shown. Here instead of simply having an electrical connection from the microchannel to the trans nanopore reservoir there is a power source inserted into the connection. This power source can be used to supply the current for translocation. Thus, the connection into the third reservoir can be the second translocation electrode. During short-circuiting of the nanopore the power source could be on but supplying zero volts to allow for current to flow and short-circuit the nanopore. In this configuration switch $S_j$ is optional.

Figure 4C:
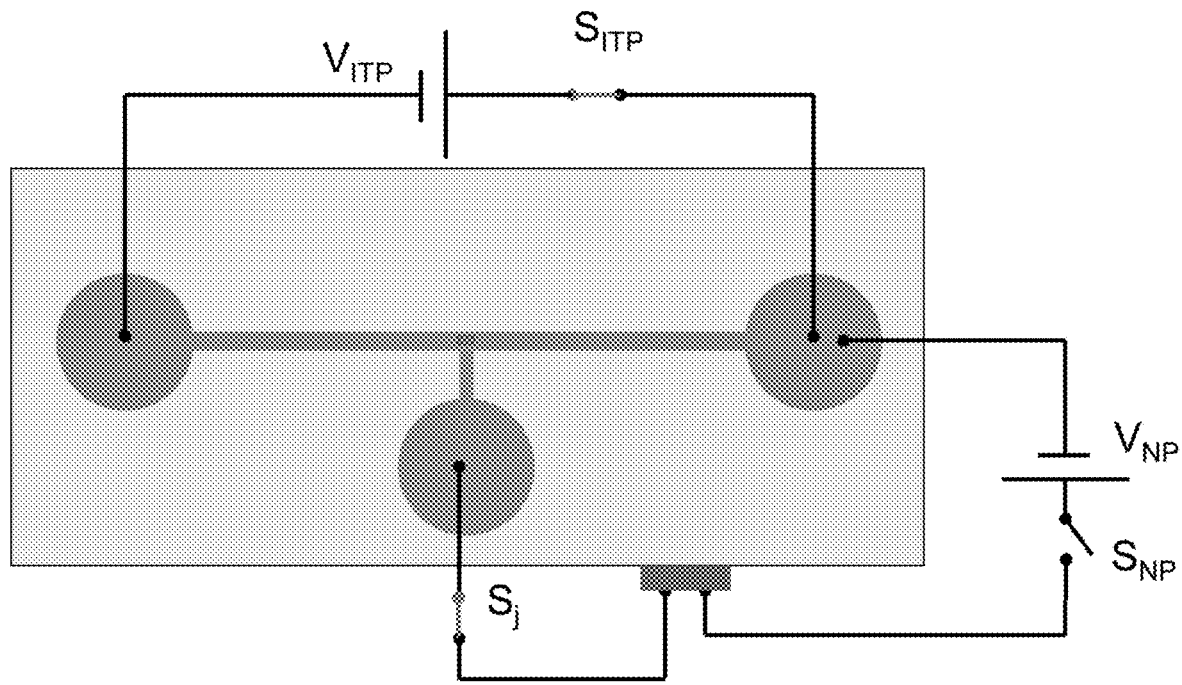
Figure 4D:
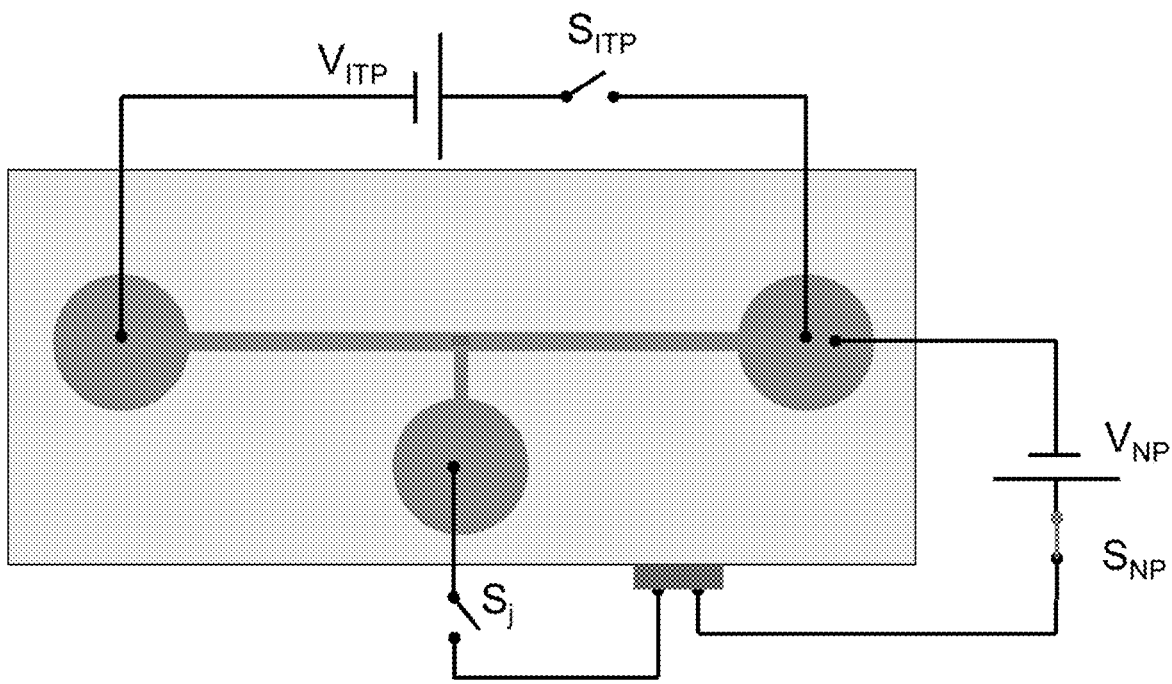

FIGS. 4C-D show yet another embodiment in which the nanopore is short-circuited. Similar to the embodiment in 4A, 4C shows a third reservoir that is in electrical contact with the trans nanopore reservoir. In 4C the configuration is shown with the switches in positions that allow for electrokinetic focusing. The ITP switch ($S_{ITP}$) is closed so that current can run from through the microchannel. The $S_j$ switch is also closed so that the nanopore is short circuited by the third reservoir. FIG. 4D shows the same embodiment, but in a configuration for nanopore translocation. The nanopore switch $S_{NP}$ is closed so that there is a current to induce translocation, but the $S_j$ is open so that the nanopore is not short-circuited. The switches are optional, but their inclusion may reduce electrical noise in the system.

Kits and Systems

Kits comprising the device of the invention are also provided. In some embodiments, the kit comprises: the device of the invention, a solution LE ion and a solution of TE ion. In some embodiments, the kit comprises instructions for modifying/making LE and/or TE that is suitable for a molecule of interest. In some embodiments, the kit comprises instructions for the running of the device of the invention.

In some embodiments, the kit further comprising at least one probe. In some embodiments, the probe binds to the molecule of interest. In some embodiments, the probe is selected from: a DNA probe, a peptide nucleic acid (PNA) probe, a Morpholino probe, a protein probe and a combination thereof.

Systems comprising the device of the invention are also provided. In some embodiments, the system further comprises at least one direct current power source for generating an electric field between electrodes of the device. In some embodiments, the system comprises at least two direct current power sources, at least a first and a second power source. In some embodiments, one power source provides an electric filed for focusing and a second power source provides an electric field for translocation. In some embodiments, the first power source generates an electric field between the first and second electrodes and the second power source generates an electric field between and electrode and the third electrode. This other electrode may be the fourth electrode or either the first or second electrode.

In some embodiments, the system further comprises a control unit or computer. In some embodiments, the control unit or computer is for performing at least one of: monitoring a position of the molecule of interest within the microchannel; stopping current running between the first and second electrodes; activating current between an electrode and the third electrode; capturing the molecule of interest proximal to the nanopore; releasing a molecule of interest captured proximal to the nanopore, and analyzing the molecule of interest as it passes through the nanopore. In some embodiments, the control unit or computer is for performing at least one of: monitoring a position of the molecule of interest within the microchannel; switching between running current between the first and second electrodes and between an electrode and the third electrode; and analyzing the molecule of interest as it passes through the nanopore. In some embodiments, the control unit or computer is for monitoring a position of the molecule of interest within the microchannel. In some embodiments, the control unit or computer is for switching between running current between the first and second electrodes and between an electrode and the third electrode. In some embodiments, the control unit or computer is for stopping the focusing current. In some embodiments, the control unit or computer is for activating the translocation current. In some embodiments, the control unit or computer is for capturing the molecule of interest proximal to the nanopore. In some embodiments, the control unit or computer is for closing valves to capture the molecule of interest proximal to the nanopore. In some embodiments, the control unit or computer is for analyzing the molecule of interest as it passes through the nanopore. In some embodiments, the analyzing comprises sequencing of the molecule.

As used herein, the term "about" when combined with a value refers to plus and minus 10% of the reference value. For example, a length of about 1000 nanometers (nm) refers to a length of 1000 nm+−100 nm.

It is noted that as used herein and in the appended claims, the singular forms "a," "an," and "the" include plural referents unless the context clearly dictates otherwise. Thus, for example, reference to "a polynucleotide" includes a plurality of such polynucleotides and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Various embodiments and aspects of the present invention as delineated hereinabove and as claimed in the claims section below find experimental support in the following examples.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A device for detecting a molecule of interest comprising:
   a. a nanopore apparatus, said nanopore apparatus comprising at least one ion-conducting nanopore;
   b. an electrokinetic focusing apparatus, said electrokinetic focusing apparatus comprising a microchannel, a first electrode and a second electrode, wherein said first and second electrodes are configured to produce an electric field in said microchannel;
   c. at least one sensor or capturing element configured for at least one of:
      i. detecting a position of said molecule of interest within said microchannel; and
      ii. capturing said molecule of interest in a region of said microchannel proximal to said nanopore;
   wherein said electrokinetic focusing apparatus and said nanopore apparatus are in fluidic contact via said nanopore and wherein at least one of:
      i. said capture element comprises at least 2 valves proximal to said nanopore, wherein said valves are configured to enclose fluid in said microchannel proximal to said nanopore;
      ii. said capture element comprises an element that binds said molecule of interest or a moiety attached thereto, optionally wherein a region of said capturing element, or said moiety attached thereto, is configured to be cleaved; and
      iii. said sensor or capture element is configured to turn off said electric field produced by said first and second electrodes, when said molecule of interest is proximal to said nanopore.

2. The device of claim 1, wherein said electrokinetic focusing apparatus
   a. further comprises a first and a second fluidic reservoir connected by said microchannel and said first and second electrodes are configured to electrically contact fluid placed in said first reservoir and fluid placed in said second reservoir, respectively; or
   b. is an isotachophoresis (ITP) apparatus.

3. The device of claim 1, wherein said nanopore apparatus further comprises a third fluidic reservoir and a third electrode configured to electrically contact fluid placed in said third reservoir, and optionally a fourth electrode configured to generate an electrical field with said third electrode.

4. A method for single-molecule detection of a molecule of interest, the method comprising electrokinetically focusing said molecule of interest to a location proximal to a nanopore, wherein said electrokinetically focusing comprises
 a. loading the device of claim 3 with a first electrolyte solution of effective ion mobility higher than said molecule of interest (LE) into said first reservoir, a second electrolyte solution of effective ion mobility lower than said molecule of interest (TE) into said second reservoirs and said microchannel and a third electrolyte solution of conductivity equal to or greater than the conductivity of said TE and said LE into said third reservoir;
 b. adding a solution comprising said molecule of interest to any one of:
  i. said TE,
  ii. said LE, and
  iii. a contact zone between said TE and said LE;
 c. running direct current between said first and said second electrodes for a period of time sufficient for said molecule of interest to be proximal to said nanopore;
 inducing the movement of said molecule of interest through said nanopore and detecting said molecule of interest as it passes through said nanopore, thereby detecting single molecules of a molecule of interest.

5. The device of claim 1, wherein said nanopore apparatus further comprises a detector configured to detect said single-molecule as it passes through said at least one nanopore, optionally wherein said detector is an optical detector or an electrical detector; or
 wherein said detecting a position of said molecule of interest comprises at least one of:
 a. directly detecting said molecule of interest or a moiety attached thereto;
 b. optically detecting changes in a fluid in said microchannel; and
 c. detecting electrical changes in said microchannel.

6. The device of claim 5, wherein said optically detecting comprises detecting at least one of a fluorochrome in said fluid, a dye in said fluid, absorbance of said fluid, refraction of said fluid, and interference of said fluid, or wherein said detecting electrical changes comprises detecting at least one of, voltage, current, resistance, conductivity and impedance in said microchannel.

7. The device of claim 1, wherein said fluid in said first reservoir is an electrolyte solution of effective ion mobility higher than said molecule of interest (LE) and said fluid in said second reservoir is an electrolyte solution of effective ion mobility lower than said molecule of interest (TE).

8. The device of claim 7 wherein said LE comprises between 50 and 500 mM of monovalent strong base cations, optionally wherein said cations are selected from potassium ions (K+) sodium ions (Na+) and lithium ions (Li+).

9. The device of claim 1, wherein said microchannel is configured such that said nanopore is sufficiently distanced from said first and second electrodes to allow for at least an 100× increase in concentration of said molecule of interest in a region proximal to said nanopore as compared to a concentration of said molecule of interest when deposited in said device.

10. A kit or system comprising,
 the device of claim 1, and
 a. a solution of high effective mobility leading electrolyte (LE) ion, and a solution of low effective mobility leading electrolyte (TE) ion; or
 b. at least one direct current power source for generating an electric field between electrodes of said device.

11. The kit or system of claim 10, further comprising a control unit or computer for performing at least one of,
 a. monitoring a position of said molecule of interest within said microchannel;
 b. stopping current running between said first and second electrodes;
 c. activating current between an electrode and said third electrode;
 d. capturing said molecule of interest proximal to said nanopore;
 e. releasing a molecule of interest captured proximal to said nanopore and
 f. analyzing said molecule of interest as it passes through said nanopore, optionally wherein said analyzing comprises sequencing of said molecule.

12. The device of claim 1, wherein proximal to said nanopore is within 100 microns (μm) of said nanopore.

13. A device for detecting a molecule of interest, comprising:
 a. an electrokinetic focusing apparatus, said electrokinetic focusing apparatus comprising a microchannel, a first electrode and a second electrode, wherein said first and second electrodes are configured to produce an electric field in said microchannel
 b. a nanopore apparatus, said nanopore apparatus comprising at least one ion-conducting nanopore, a first fluidic reservoir and a third electrode configured to electrically contact fluid placed in said first reservoir;
 c. an element that electrically connects said microchannel to said first reservoir; and
 d. at least one sensor or capturing element configured for at least one of:
  i. detecting a position of said molecule of interest within said microchannel; and
  ii. capturing said molecule of interest in a region of said microchannel proximal to said nanopore, optionally wherein proximal to said nanopore is within 100 microns (μm) of said nanopore;
 wherein said electrokinetic focusing apparatus and said nanopore apparatus are in fluidic contact via said nanopore and wherein said element comprises a second reservoir and said second reservoir is electrically connected, but not fluidically connected, to said first reservoir.

14. The device of claim 13, wherein said element comprises a second microchannel and wherein said second microchannel fluidically connects said first microchannel to said first reservoir or said second reservoir.

15. The device of claim 13, further comprising, a fast-acting switch configured to switch from conducting current between said first and second electrodes and conducting current between said third electrode and another electrode.

16. The device of claim 15, wherein said fast-acting switch
 a. is selected from an optically isolated metal oxide semiconductor field effect transistor (OPFET) switch and a bipolar junction (BPJ);
 b. produces output noise that is not more than 30% of a nanopore measuring signal; or
 c. comprises high electric isolation.

17. The device of claim 13, wherein said electrokinetic focusing apparatus
   a. further comprises a third and a fourth fluidic reservoir connected by said microchannel and said first and second electrodes are configured to electrically contact fluid placed in said third reservoir and fluid placed in said fourth reservoir, respectively; or
   b. is an isotachophoresis (ITP) apparatus.

18. A method for single-molecule detection of a molecule of interest, the method comprising electrokinetically focusing said molecule of interest to a location proximal to a nanopore, inducing the movement of said molecule of interest through said nanopore and detecting said molecule of interest as it passes through said nanopore, thereby detecting single molecules of a molecule of interest.

19. The method of claim 18, further comprising halting the movement of said molecule in the direction of said first and second electrodes while proximal to said nanopore wherein said halting comprises at least one of:
   a. removal of said direct current;
   b. enclosing the area proximal to said nanopore;
   c. activating counter-flow in a direction opposite to said movement; and
   d. capturing said molecule or a moiety attached thereto to a capture element in a region proximal to said nanopore.

20. The method of claim 19, further comprising releasing said molecule from said capture element, optionally wherein said releasing comprises cleaving said capture element or said moiety; or wherein said inducing comprises running direct current from an electrode to said third electrode and said halting and inducing are synchronized by a fast-acting switch.

* * * * *